US008344018B2

(12) United States Patent
Graupe et al.

(10) Patent No.: US 8,344,018 B2
(45) Date of Patent: Jan. 1, 2013

(54) OXINDOLYL INHIBITOR COMPOUNDS

(75) Inventors: Michael Graupe, Pacifica, CA (US); Chandrasekar Venkataramani, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 135 days.

(21) Appl. No.: 12/997,487

(22) PCT Filed: Jul. 14, 2009

(86) PCT No.: PCT/US2009/050595
§ 371 (c)(1),
(2), (4) Date: Feb. 22, 2011

(87) PCT Pub. No.: WO2010/009166
PCT Pub. Date: Jan. 21, 2010

(65) Prior Publication Data
US 2011/0135594 A1 Jun. 9, 2011

Related U.S. Application Data

(60) Provisional application No. 61/080,415, filed on Jul. 14, 2008.

(51) Int. Cl.
*A01N 43/38* (2006.01)
*A61K 31/40* (2006.01)
(52) U.S. Cl. ........ 514/418; 514/411; 544/144; 548/151; 548/181; 548/465
(58) Field of Classification Search ............... 514/418, 514/411; 544/144; 548/151, 181, 465
See application file for complete search history.

(56) References Cited

U.S. PATENT DOCUMENTS

| | | | |
|---|---|---|---|
| 5,760,246 A | 6/1998 | Biller et al. | |
| 6,403,588 B1 | 6/2002 | Hayakawa et al. | |
| 6,858,641 B2 * | 2/2005 | Roth et al. | 514/415 |
| 7,253,204 B2 | 8/2007 | Delorme et al. | |
| 2002/0168761 A1 | 11/2002 | Gour et al. | |
| 2004/0006011 A1 | 1/2004 | Gour et al. | |
| 2005/0054850 A1 | 3/2005 | Wu et al. | |
| 2005/0187266 A1 | 8/2005 | Su | |
| 2005/0234066 A1 | 10/2005 | Bailey et al. | |
| 2005/0288282 A1 | 12/2005 | Delorme et al. | |
| 2006/0293320 A1 | 12/2006 | Schmitz et al. | |
| 2007/0093492 A1 | 4/2007 | Jiaang et al. | |
| 2007/0213330 A1 | 9/2007 | Delorme et al. | |
| 2009/0005374 A1 | 1/2009 | Melvin, Jr. et al. | |
| 2009/0076021 A1 | 3/2009 | Plato | |
| 2010/0009990 A1 | 1/2010 | Venkataramani | |
| 2010/0022543 A1 | 1/2010 | Melvin, Jr. et al. | |
| 2010/0029638 A1 | 2/2010 | Melvin, Jr. et al. | |
| 2010/0310500 A1 | 12/2010 | Graupe et al. | |
| 2010/0311794 A1 | 12/2010 | Venkataramani | |

FOREIGN PATENT DOCUMENTS

| | | |
|---|---|---|
| CA | 2644933 A1 | 9/2007 |
| EP | 0847992 A1 | 6/1998 |
| EP | 1277754 A1 | 1/2003 |
| JP | 2003-313126 A | 11/2003 |
| JP | 2004-002826 A | 1/2004 |
| JP | 2007-001885 A | 1/2007 |
| WO | WO-97/26240 A1 | 7/1997 |
| WO | WO-00/18733 A1 | 4/2000 |
| WO | WO-01/14375 A1 | 3/2001 |
| WO | WO-01/19788 A2 | 3/2001 |
| WO | WO-01/53331 A2 | 7/2001 |
| WO | WO-01/56989 A2 | 8/2001 |
| WO | WO-01/83481 A1 | 11/2001 |
| WO | WO-02/00651 A2 | 1/2002 |
| WO | WO-02/26712 A2 | 4/2002 |
| WO | WO-02/34748 A1 | 5/2002 |
| WO | WO-02/46170 A2 | 6/2002 |
| WO | WO-02/065979 A2 | 8/2002 |
| WO | WO-02/066480 A2 | 8/2002 |
| WO | WO-02/066481 A1 | 8/2002 |
| WO | WO-03/000682 A1 | 1/2003 |
| WO | WO-03/000689 A1 | 1/2003 |
| WO | WO-03/002524 A2 | 1/2003 |
| WO | WO-03/031446 A1 | 4/2003 |
| WO | WO-03/041649 A2 | 5/2003 |
| WO | WO-03/084948 A1 | 10/2003 |
| WO | WO-03/084997 A1 | 10/2003 |

(Continued)

OTHER PUBLICATIONS

International Preliminary Report for International Application No. PCT/US2009/050595, International Filing Date Jul. 14, 2009, mailed Jan. 27, 2011.

Office Action for EP Patent Application No. 09790416.3, mailed Mar. 3, 2011.

Acharya et al. (2005) "Rational Development of Histone Deacetylase Inhibitors as Anticancer Agents" *A Review, Molecular Pharmacology* 68:917-932.

Alam et al. (2007) "Synthesis and SAR of Aminopyriidines as Novel c-Jun N-terminal Kinase (JNK) Inhibitors" *Science Direct, Bioorganic & Medicinal Chemistry Letters* 17:3463-3467.

Arbiser, J.L. (2007) "Why Targeted Therapy Hasn't Worked in Advanced Cancer", *The Journal of Clinical Investigation*, vol. 17, No. 10 pp. 2762-2765.

(Continued)

*Primary Examiner* — Andrew D Kosar
*Assistant Examiner* — Valerie Rodriguez-Garcia
(74) *Attorney, Agent, or Firm* — J. Ellin Hartrum

(57) ABSTRACT

A compound of general Formula (I) having histone deacetylase (HDAC) and/or CDK inhibitory activity, a pharmaceutical composition comprising the compound, and a method useful to treat diseases using the compound. (Formula should be inserted here) Formula (I)

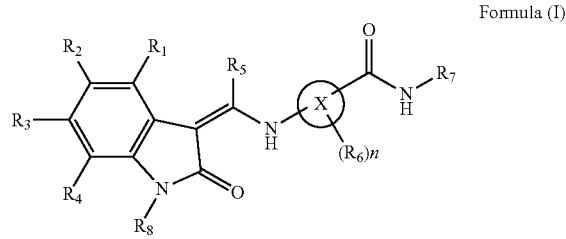

Formula (I)

12 Claims, No Drawings

FOREIGN PATENT DOCUMENTS

| | | |
|---|---|---|
| WO | WO-03/099221 A2 | 12/2003 |
| WO | WO-03/099817 A1 | 12/2003 |
| WO | WO-03/103151 A1 | 12/2003 |
| WO | WO-2004/021989 A2 | 3/2004 |
| WO | WO-2004/035525 A1 | 4/2004 |
| WO | WO-2004/039325 A2 | 5/2004 |
| WO | WO-2004/041191 A2 | 5/2004 |
| WO | WO-2004/048343 A1 | 6/2004 |
| WO | WO-2004/060318 A2 | 7/2004 |
| WO | WO-2004/069133 A2 | 8/2004 |
| WO | WO-2004/069803 A2 | 8/2004 |
| WO | WO-2004/076452 A1 | 9/2004 |
| WO | WO-2004/080390 A2 | 9/2004 |
| WO | WO-2004/084901 A1 | 10/2004 |
| WO | WO-2004/092115 A2 | 10/2004 |
| WO | WO-2004/092145 A1 | 10/2004 |
| WO | WO-2004/110350 A1 | 12/2004 |
| WO | WO-2005/006945 A2 | 1/2005 |
| WO | WO-2005/030140 A2 | 4/2005 |
| WO | WO-2005/030705 A1 | 4/2005 |
| WO | WO-2005/046594 A2 | 5/2005 |
| WO | WO-2005/054850 A2 | 6/2005 |
| WO | WO-2005/060571 A2 | 7/2005 |
| WO | WO-2005/070180 A2 | 8/2005 |
| WO | WO-2005/077368 A2 | 8/2005 |
| WO | WO-2005/077373 A2 | 8/2005 |
| WO | WO-2005/082871 A2 | 9/2005 |
| WO | WO-2005/092899 A1 | 10/2005 |
| WO | WO-2005/102318 A1 | 11/2005 |
| WO | WO-2005/102325 A1 | 11/2005 |
| WO | WO-2005/102326 A2 | 11/2005 |
| WO | WO-2005/102346 A1 | 11/2005 |
| WO | WO-2005/102455 A2 | 11/2005 |
| WO | WO-2005/103022 A1 | 11/2005 |
| WO | WO-2005/112920 A1 | 12/2005 |
| WO | WO-2005/115304 A2 | 12/2005 |
| WO | WO-2005/115385 A1 | 12/2005 |
| WO | WO-2006/010750 A1 | 2/2006 |
| WO | WO-2006/038001 A1 | 4/2006 |
| WO | WO-2006/044509 A1 | 4/2006 |
| WO | WO-2006/058007 A2 | 6/2006 |
| WO | WO-2006/058905 A1 | 6/2006 |
| WO | WO-2006/064251 A1 | 6/2006 |
| WO | WO-2006/070943 A1 | 7/2006 |
| WO | WO-2006/077401 A1 | 7/2006 |
| WO | WO-2006/104983 A1 | 10/2006 |
| WO | WO-2006/108059 A1 | 10/2006 |
| WO | WO-2006/122011 A2 | 11/2006 |
| WO | WO-2007/008664 A1 | 1/2007 |
| WO | WO 2007/008895 * | 1/2007 |
| WO | WO-2007/026251 A2 | 3/2007 |
| WO | WO-2007/030362 A1 | 3/2007 |
| WO | WO-2007/036732 A1 | 4/2007 |
| WO | WO-2007/037187 A1 | 4/2007 |
| WO | WO-2007-040440 A1 | 4/2007 |
| WO | WO-2007/055941 A2 | 5/2007 |
| WO | WO 2007/062078 * | 5/2007 |
| WO | WO-2007/076034 A2 | 7/2007 |
| WO | WO-2007/076035 A2 | 7/2007 |
| WO | WO-2007/079185 A2 | 7/2007 |
| WO | WO-2007/087129 A2 | 8/2007 |
| WO | WO-2007/087717 A1 | 8/2007 |
| WO | WO-2007/093492 A1 | 8/2007 |
| WO | WO-2007/095124 A2 | 8/2007 |
| WO | WO-2007/100795 A2 | 9/2007 |
| WO | WO-2007/106192 A2 | 9/2007 |
| WO | WO-2007/127137 A2 | 11/2007 |
| WO | WO-2007/135036 A1 | 11/2007 |
| WO | WO-2008/033743 A1 | 3/2008 |
| WO | WO-2009/002534 A1 | 12/2008 |
| WO | WO-2009/079391 A1 | 6/2009 |
| WO | WO-2010/009139 A2 | 1/2010 |
| WO | WO-2010/009155 A2 | 1/2010 |
| WO | WO-2010/009166 A1 | 1/2010 |
| WO | WO-2010/014611 A1 | 2/2010 |

OTHER PUBLICATIONS

Buggy et al. (2006) "CRA-024781: A Novel Synthetic Inhibitor of Histone Decetylase Enzymes with Antitumor Activity In Vitro and In Vivo" *Mol .Cancer Ther.* 5:1309-1317.

Bush et al. (2009) "Targeting Histone Deacetylases for Heart Failure" *Myogen, Inc.* 1-39.

Feng et al. (2006) "Synthesis and SAR of 2-(4-fluorophenyl)-3-pyrimidin-4-ylimidazo[1,2-a]pyridine Derivatives as Anticoccidial Agents" *Science Direct, Bioorganic & Medicinal Chemistry Letters* 16:5978-5981.

Fischer, B. et al. (2007) "Targeting Receptor Tyrosine Kinase Signalling in Small Cell Lung Cancer (SCLC): What Have We Learned So Far?", *Cancer Treatment Reviews*, vol. 33, pp. 391-406.

Gudmundsson et al. (2007) "Imidazo[1,2-a]ayridines With Potent Activity Against Herpesviruses" *Scienc Direct, Bioorganic & Medicinal Chemistry Letters* 17:2735-2739.

Hayakawa et al. (2007) "Synthesis and Biological Evaluation of Imidazol[1,2-a]pyridine Derivatives As Novel PI3 Kinase p110a Inhibitors" *Science Direct, Bioorganic & Medicinal Chemistry* 15:403-412.

International Search Report for PCT/US2008/007963, International Filing Date Jun. 26, 2008, mailed Oct. 1, 2008.

International Search Report for PCT/US2008/086643, International Filing Date Dec. 12, 2008, mailed Mar. 23, 2009.

International Search Report for PCT/US2009/050558, International Filing Date Jul. 14, 2009, mailed Oct. 12, 2009.

International Search Report for PCT/US2009/050577, International Filing Date Jul. 14, 2009, mailed Nov. 11, 2009.

International Search Report for PCT/US2009/050595, International Filing Date Jul. 14, 2009, mailed Nov. 18, 2009.

International Search Report for PCT/US2009/051964, International Filing Date Jul. 28, 2009, mailed Oct. 2, 2009.

International Search Report for PCT/US2010/037647, International Filing Date Jun. 7, 2010, mailed Nov. 9, 2010.

Liang et al. (2007) "Synthesis and SAR Studies of Potent Imidazopyridine Anticoccidial Agents" *Science Direct, Bioorganic & Medicinal Chemistry Letters* 17:3558-3561.

Madhusudan, S. et al. (2004) "Tyrosine Kinase Inhibitors in Cancer Therapy", *Clinincal Biochemistry*, vol. 37, 00.618-635.

Mahboobi et al. (2007) "2-Aroylindoles and w-Arolbenzofurans with N-Hydroxyacrylamide Substructures as a Novel Series of Rationally Designed Histone Deacetylase Inhibitors" *American Chemical Society* A-N.

Marcou et al. (2007) "Optimizing Fragment and Scaffold Docking by Use of Molecular Interaction Fingerprints" *Journal of Chemistry Inf. Model* 47(1):195-207.

Moradeli et al. (2005) "Histone Deacetylase Inhibitors" *Latest Developments, Trends, and Prospects, Current Medicinal Chemistry—Anti-Cancer Agents* 529-560.

Paris et al. (2008) "Histone Deacetylase Inhibitors: From Bench to Clinic" *Journal of Medicinal Chemistry* A-Y.

Park et al. (2007) "A Simple and Efficient Docking Method to the Cyclin-Dependent Kinase 2" *Bull. Korean Chemistry Soc.* 28(2):211-219.

Price et al. (2007) Histone Deacetylase Inhibitors: An Analysis of REcent Patenting Activity *Informa UK Ltd, Expert Opinion, Ther. Patents* 745-765.

Rosato et al. (2003) "The Histone Deacetylase Inhibitor MS-275 Promotes Differentation or Apoptosis in Human Leukemia Cells Through a Process Regulated by Generation of Reactive Oxygen Species and Induction of p21" *Cancer Research* 63:3637-3645.

U.S. Office Action for U.S. Appl. No. 12/146,894, mailed May 10, 2010.

U.S. Office Action for U.S. Appl. No. 12/747,159, mailed Dec. 10, 2010.

Vadivelan et al. (2007) "Virtual Screening Studies to Design Patent CDKS2-Cyclin A Inhibitors" *Journal of Chemistry Inf. Model* 47(4):205-218.

Vigushin et al. (2004) "Targeted Histone Deacetylase Inhibition for Cancer Therapy" *Current Cancer Drug Targets* 4(2):205-218.

Lee, M. et al. (2003) "Molecular Targets for Cell Cycle Inhibition and Cancer Therapy", *Expert Opinion on Therapeutic Patents* 17(7):745-765.

\* cited by examiner

OXINDOLYL INHIBITOR COMPOUNDS

CROSS REFERENCE TO RELATED APPLICATION

This application claims the benefit of U.S. provisional application Ser. No. 61/080,415 filed Jul. 14, 2008. The disclosure of the application is hereby incorporated by reference.

FIELD

The present invention generally relates to a compound having enzyme inhibitory activity, pharmaceutical compositions comprising the compound, and methods useful for treating diseases.

BACKGROUND

Histones are protein components making up chromatin in association with DNA. Histones are subject to covalent modifications of various enzymes such as, for example, histone deacetylase (HDAC), histone methyltransferase (HMT) and histone acetyltransferase (HAT). Covalent modifications of core histones influence protein-protein interaction and protein access to DNA.

HDACs catalyze deacetylation of lysine residues on histones and other proteins. It is known that low levels of histone-acetylation are associated with repression of gene expression. Therefore, abnormal HDAC activities could destroy the delicate balance in cell regulation. The HDACs belong to four structurally and functionally different phylogenetic classes: class I (HDAC-1, -2, -3, and -8) compounds are closely related to yeast RPD3; class IIa (HDAC-4, -5, -7, and -9) and class IIb (HDAC-6 and -10) share domains with yeast HDAC-1; class IV, recently described (comprising HDAC-11), exhibits properties of both class I and class II HDACs. All the above HDACs are zinc dependent proteases. Class III HDACs have been identified on the basis of sequence similarity with Sir2, a yeast transcription repressor, and require the cofactor $NAD^+$ for their deacetylase function. See, for example, Marielle Paris et al., *Histone Deacetylase Inhibitors: From Bench to Clinic*, JOURNAL OF MEDICINAL CHEMISTRY 51(11): 3330-3330 (2008).

It has been reported that HDAC activities play an important role in a variety of human disease states. Accordingly, an HDAC inhibitor can provide therapeutic benefits to a broad range of patients. Due to the therapeutic significance, various types of HDAC inhibitors have been developed to date. See, for example, Moradeli et al., *Histone Deacetylase Inhibitors Latest Developments, Trends, and Prospects*, CURR. MED. CHEM.: ANTI-CANCER AGENTS 5(5):529-560 (2005).

Cyclin-dependent kinases (CDKs) are protein kinase enzymes controlling transcription and mRNA processing for the regulation of the cell cycle. CDKs belong to a group of serine/threonine kinases phosphorylating proteins on serine and threonine amino acid residues. A CDK is activated by association with a cyclin forming a cyclin-dependent kinase complex. The CDK family has been identified to include at least 9 members, i.e., CDK1, CDK2, CDK3, CDK4, CDK5, CDK6, CDK7, CDK8 and CDK9, and CDKs pair with a specific cyclin in the various phases of the cell cycle for the progression. CDKs are considered a target for anti-cancer medication since the enzymes are major control switches for the cell cycle.

WO 2005/092899 mentions a series of compounds useful for inhibiting HDAC enzymatic activity where the compounds are amino or hydroxyl substituted aniline derivatives attached to various cyclic groups.

There is a continued need to develop new inhibitors to provide appropriate therapy for a variety of disease conditions implicated in HDAC and/or CDK activity.

SUMMARY

In various embodiments, a compound having HDAC inhibitory activity, a composition comprising the compound, and a method useful to treat diseases arising from abnormal cell proliferation or differentiation are provided.

The compound is of Formula (I) or a pharmaceutically acceptable salt thereof:

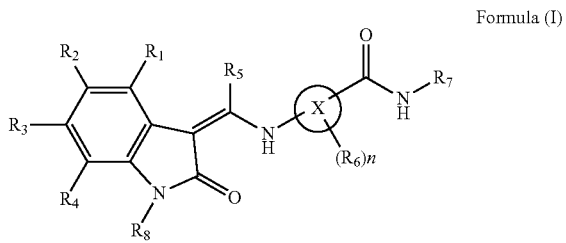

Formula (I)

wherein $R^1$, $R^2$, $R^3$ and $R^4$ are independently selected from the group consisting of H, halo, nitro, cyano, hydroxy, hydroxyalkyl, haloalkyl, haloalkoxy, amino, aminoalkyl, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N-($C_{1-10}$ alkyl)amino, N-(heterocyclyl $C_{1-10}$ alkyl)amino, N,N-($C_{1-10}$ alkyl)$_2$amino, $C_{1-10}$ alkanoylamino, N—($C_{1-10}$ alkyl)carbamoyl, N,N-($C_{1-10}$ alkyl)$_2$carbamoyl, $C_{1-10}$ alkyl-S(O)$_a$ wherein a is 0, 1 or 2, $C_{1-6}$ alkoxycarbonyl, $NH_2$—S(O)$_2$NH—, N-($C_{1-10}$ alkyl) sulphamoyl, N,N-($C_{1-10}$ alkyl)$_2$sulphamoyl, aryl, aryloxy, arylthio, heteroaryl, heteroaryloxy, cycloalkyl, cycloalkyloxy, heterocyclyl, heterocyclyl(C═O)—, heterocyclyloxy and heterocyclylthio; wherein each of $R^1$, $R^2$, $R^3$ and $R^4$ is optionally substituted by one or more A where such an optional substitution is chemically feasible, or $R^3$ and $R^4$ are as defined above, and $R^1$ and $R^2$ together form a cyclic moiety to make a fused ring together with the oxindole ring drawn in Formula (I). In an embodiment, the cyclic moiety formed by $R^1$ and $R^2$ contains only carbon ring atoms; in another embodiment, the cyclic moiety contains one or more heteroatoms selected from N, O and S. The cyclic moiety itself is partially or totally unsaturated, and is optionally substituted by one or more substituents selected from those defined above for $R^1$, $R^2$, $R^3$ and $R^4$ groups, each of which is optionally substituted by one or more A where such an optional substitution is chemically feasible, or $R^1$ and $R^4$ are as defined above, and $R^3$ and $R^2$ together form a cyclic moiety to make a fused ring together with the oxindole ring drawn in Formula (I). In an embodiment, the cyclic moiety formed by $R^3$ and $R^2$ contains only carbon ring atoms; in another embodiment, the cyclic moiety contains one or more heteroatoms selected from N, O and S. The cyclic moiety itself is partially or totally unsaturated, and is optionally substituted by one or more substituents selected from those defined above for $R^1$, $R^2$, $R^3$ and $R^4$ groups, each of which is optionally substituted by one or more A where such an optional substitution is chemically feasible;

R[5] is selected from the group consisting of H, halo, haloalkyl, amino, $C_{1-10}$ alkyl, N—($C_{1-10}$ alkyl)amino, N,N-($C_{1-10}$ alkyl)$_2$ amino, alkoxyalkyl, alkylaminoalkyl, and cycloalkyl, wherein R[5] is optionally substituted by one or more B where such an optional substitution is chemically feasible;

X is phenyl, 5-membered heteroaryl, or 6-membered heteroaryl, wherein the heteroaryl contains one or more heteroatoms selected from N, S and O;

R[6] represents one or more optional non-hydrogen substituents on ring X. When present, each R[6] is independently selected from hydroxy, halo, nitro, cyano, trifluoromethyl, trifluoromethoxy, amino, carboxyl, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N-($C_{1-10}$ alkyl)amino, N,N-($C_{1-10}$ alkyl)$_2$ amino, $C_{1-10}$ alkanoylamino, N-($C_{1-10}$ alkyl)carbamoyl, N,N-($C_{1-10}$ alkyl)$_2$ carbamoyl, $C_{1-10}$ alkyl-S(O)$_a$ wherein a is 0, 1 or 2, NH$_2$—S(O)$_2$NH—, N-($C_{1-10}$ alkyl)sulphamoyl, N,N-($C_{1-10}$ alkyl)$_2$sulphamoyl, cycloalkyl, heterocyclyl, aryl and heteroaryl;

n is the number of non-hydrogen substituents R[6] on the ring X and can be 0, 1, 2, 3, or 4. The maximum value of n depends on the nature of the ring X;

R[7] is hydroxy, aryl, or heteroaryl, wherein aryl or heteroaryl are substituted with —NH$_2$ or —OH and aryl or heteroaryl is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl;

R[8] is H, alkyl, alkanoyl, or cycloalkyl; and

A and B are independently selected from halo, nitro, cyano, hydroxy, oxo, hydroxyalkyl, haloalkyl, haloalkoxy, amino, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkoxyalkyl, $C_{1-10}$ alkanoyl, $C_{1-10}$ alkanoyloxy, N-(heterocyclyl $C_{1-10}$ alkyl)amino, N-($C_{1-10}$ alkyl)amino, N,N-($C_{1-10}$ alkyl)$_2$amino, $C_{1-10}$ alkanoylamino, N-($C_{1-10}$ alkyl)carbamoyl, N,N-($C_{1-10}$ alkyl)$_2$carbamoyl, $C_{1-10}$ alkyl-S(O)$_a$ wherein a is 0, 1 or 2, $C_{1-10}$ alkoxycarbonyl, N-($C_{1-10}$ alkyl)sulphamoyl, N,N-($C_{1-10}$ alkyl)$_2$sulphamoyl, H$_2$NS(O)$_2$NH—, N-($C_{1-10}$ alkyl)NHS(O)$_2$NH—, N,N-($C_{1-10}$ alkyl)$_2$NS(O)$_2$NH—, aryl, aryloxy, arylthio, heteroaryl, heteroaryloxy, cycloalkyl, cycloalkyloxy, heterocyclyl, heterocyclyl(C=O)—, heterocyclyloxy and heterocyclylthio.

Non-limiting examples of A and B include halo, alkyl, nitro, cyano, hydroxy, oxo, cycloalkyl, trifluoromethoxy, trifluoromethyl, trifluoroethyl, amino, carboxyl, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-morpholinylethylamino, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl, aryl, heterocyclylcycloalkyl and heteroaryl.

In the definitions herein of R[1], R[2], R[3], R[4], R[5], R[6], R[8], A and B the carbon ranges for the groups alkyl, alkenyl, alkynyl, alkoxy, alkanoyl, alkanoyloxy, alkanoylamino, and the like include all ranges encompassed in the recited ranges $C_{1-10}$ and $C_{2-10}$. For example, in non-limiting fashion $C_{1-10}$ and $C_{2-10}$ include a disclosure of $C_{1-6}$ and $C_{1-3}$. In various embodiments, $C_{1-10}$ carbon-chain containing groups such as $C_{1-10}$ alkyl, $C_{2-10}$ alkenyl, $C_{2-10}$ alkynyl and so forth include the respective $C_{1-6}$ and $C_{1-3}$ shorter carbon-chains such as $C_{1-6}$ alkyl, $C_{1-3}$ alkyl, $C_{2-6}$ alkenyl, $C_{2-3}$ alkenyl, $C_{2-6}$ alkynyl and $C_{2-3}$ alkynyl.

In an embodiment, at least two of R[1], R[2], R[3] and R[4] are H. In an embodiment, both R[1] and R[4] are hydrogen. In another embodiment, R[1], R[2], R[3], and R[4] are hydrogen. In various embodiments, one of R[3] and R[4] is hydrogen or both R[3] and R[4] are hydrogen.

In an embodiment, R[5] is H or methyl.

In an embodiment, R[7] is hydroxy and the compounds are characterized as hydroxamates. In another embodiment, R[7] is substituted aryl or heteroaryl and the compounds are characterized as arylamides.

In an embodiment, R[8] is H or methyl.

In an embodiment when X is phenyl, n is 0; in another embodiment, n is 1; in another embodiment, n is 2.

In an embodiment, X is phenyl. In various embodiments, the NH— and —C(O)NH—R[7] groups are disposed on the phenyl in a 1,4-configuration, where NH— is considered as the 1-position.

In an embodiment, X is thiophene. In various embodiments, the NH— and —C(O)NH—R[1] groups are disposed on the thiophene in a 2,5-configuration, where NH— is considered as the 2-position (with the S atom of the thiophene ring taken as the 1-position).

In an embodiment, X is pyridine. In various embodiments, the NH— and —C(O)NH—R[1] groups are disposed on the pyridine in a 2,5-configuration, where NH— is considered as the 2-position, or in a 3,6-configuration, where NH— is considered as the 3-position (in all cases, the N atom of the pyridine ring is taken as the 1-position).

In an embodiment, X is thiazole. In various embodiments, the NH containing moiety and —C(O)NH—R[8] groups are disposed on the thiazole in a 2,4- or 2,5-configuration, where the NH linker is considered as the 2-position (with the S atom of the thiazole ring taken as the 1-position).

In the Tables that follow, examples are given with n=0 or n=1. When n=0, the entry in the R[6] column reads H (hydrogen) to indicate that all substituents are hydrogen. When n=1, the entry in the R[6] column gives the identity and position of the single non-hydrogen substituent.

Pharmaceutical compositions comprise an HDAC and/or CDK-inhibitory effective amount of one or more compounds described above and a pharmaceutically-acceptable carrier.

Methods of inhibiting or treating diseases arising from abnormal cell proliferation and differentiation comprise administering to a subject a therapeutically effective amount of one or more compounds described herein. Other methods involve co-therapies by administering one or more of the compounds together with other anti-cancer agents.

The compounds above are more fully described in the detailed description that follows.

DETAILED DESCRIPTION

The following description is merely exemplary in nature and is not intended to limit the present disclosure, application, or uses.

DEFINITIONS

"Alkenyl" refers to a straight or branched hydrocarbyl group with at least one site of unsaturation, i.e. a carbon-carbon, sp$^2$ double bond. In an embodiment, alkenyl has from 2 to 12 carbon atoms. In some embodiments, alkenyl is a $C_2$-$C_{10}$ alkenyl group or a $C_2$-$C_6$ alkenyl group. Examples of alkenyl group include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkanoyl" is the group RC(O)—; "alkanoyloxy" is RC(O)O—; and "alkanoylamino" is RC(O)NR'—; where R is an alkyl group as defined herein, and R' is hydrogen or alkyl. In various embodiments, R is a $C_1$-$C_{10}$ alkyl group or a $C_1$-$C_6$ alkyl group.

"Alkoxy" is RO— where R is alkyl. Non-limiting examples of alkoxy groups include methoxy, ethoxy and propoxy.

"Alkoxyalkyl" refers to an alkyl moiety substituted with an alkoxy group. Examples of alkoxyalkyl groups include methoxymethyl, methoxyethyl, methoxypropyl and ethoxyethyl.

"Alkoxycarbonyl" is ROC(O)—, where R is an alkyl group as defined herein. In various embodiments, R is a $C_1$-$C_{10}$ alkyl group or a $C_1$-$C_6$ alkyl group.

"Alkyl" refers to a straight or branched chain hydrocarbyl group. In an embodiment, alkyl has from 1 to 12 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Alkylamino" refers to an amino group substituted with one or more alkyl groups. "N-(alkyl)amino" is RNH— and "N,N-(alkyl)$_2$amino" is $R_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, butylamino, dimethylamino, diethylamino, and methylethylamno.

"Alkylaminocarbonyl" is R'R"NC(O)—, where at least one of R' and R" is an alkyl group as defined herein. In various embodiments, the alkyl group is a $C_1$-$C_{10}$ alkyl group or a $C_1$-$C_6$ alkyl group.

"Alkylaminoalkyl" refers to an alkyl moiety substituted with an alkylamino group, wherein alkylamino is as defined herein. Examples of alkylaminoakyl groups include methylaminomethyl and ethylaminomethyl.

"Alkylsulfonyl" is R—S(O)$_2$—, where R is alkyl. In various embodiments, R is a $C_1$-$C_{10}$ alkyl group or a $C_1$-$C_6$ alkyl group.

"Alkynyl" refers to a straight or branched carbon-chain group with at least one site of unsaturation, i.e. a carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$ alkynyl group. Examples of alkynyl groups include acetylenic (—C≡CH) and propargyl (—$CH_2$C≡CH).

"Aryl" refers to any monocyclic, bicyclic or tricyclic carbon ring, wherein at least one ring is aromatic, or an aromatic ring system of 5 to 14 carbons atoms which includes a carbocyclic aromatic group fused with a 5- or 6-membered cycloalkyl group. Examples of aryl groups include, but are not limited to, phenyl, naphthyl, tetrahydronaphthyl and indanyl.

"Aryloxy" is RO—, where R is aryl. "Arylthio" is RS—, where R is aryl.

"Carbamoyl" is the group $NH_2$—C(O)—; the nitrogen can be substituted with alkyl groups. N-(alkyl)carbamoyl is RNH—C(O)— and N,N-(alkyl)$_2$ carbamoyl is $R_2$N—C(O)—, where the R groups are alkyl as defined herein and are the same or different. In various embodiments, R is a $C_1$-$C_{10}$ alkyl group or a $C_1$-$C_6$ alkyl group.

"Cycloalkyl" is a hydrocarbyl group containing at least one saturated or partially unsaturated ring structure, and attached via a ring carbon. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

"Cycloalkyloxy" is RO—, where R is cycloalkyl.

"Cycloalkylalkyl" refers to an alkyl moiety substituted with a cycloalkyl group, wherein cycloalkyl is as defined herein. Examples of cycloalkylalkyl groups include cyclopropylmethyl, cyclobutylmethyl, cyclopentylethyl and cyclohexylmethyl.

"Dialkylamino" refers to an RR'N— group where R and R' are independently alkyl as defined herein. Examples of dialkylamino groups include, but are not limited to, dimethylamino, diethylamino, methylethylamino and methylpropylamino. In various embodiments, R and R' are independently $C_1$-$C_{10}$ alkyl or $C_1$-$C_6$ alkyl.

"Dialkylaminoalkyl" refers to an alkyl moiety substituted with a dialkylamino group, wherein dialkylamino is as defined herein. Examples of dialkylaminoalkyl groups include, but are not limited to, dimethylaminomethyl and diethylaminomethyl.

"Feasible" refers to a structure or process that is capable of being accomplished; one that is possible, suitable, or logical. When a structure or process is "chemically feasible", that structure or process is synthetically attainable, chemically stable to the typical ambient conditions and/or contributes to favorable biological properties such as efficacy, bioavailability and minimal toxicity for the intended use.

Chemically feasible structures are bound by the rules of electron bonding, whereby bonds can only be formed between atoms that are capable of forming bonds with one another. Likewise, chemically feasible processes can only produce structures that are chemically feasible.

"Halo" refers to chloro (—Cl), bromo (—Br), fluoro (—F) or iodo (—I).

"Haloalkoxy" refers to an alkoxy group substituted with one or more halo groups and examples of haloalkoxy groups include, but are not limited to, —OCF$_3$, —OCHF$_2$ and —OCH$_2$F.

"Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl.

"Haloalkyl" refers to an alkyl moiety substituted with one or more halo groups. Examples of haloalkyl groups include —CF$_3$ and —CHF$_2$.

"Heterocyclyl" includes the heteroaryls defined below and refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

"Heterocyclyloxy" is RO—, where R is heterocyclyl. "Heterocyclylthio" is RS—, where R is heterocyclyl.

"Heterocyclylsulfonyl" is $RS(O)_2$—, where R is heterocyclyl.

"Heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S, Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroaryloxy" is RO—, where R is heteroaryl.

"Hydroxyalkoxy" refers to an alkoxy group substituted with a hydroxyl group (—OH), wherein alkoxy is as defined herein. An example of hydroxyalkoxy is hydroxyethoxy.

"Hydroxyalkyl" refers to a linear or branched monovalent $C_1$-$C_{10}$ hydrocarbon group substituted with at least one hydroxy group and examples of hydroxyalkyl groups include, but are not limited to, hydroxymethyl, hydroxyethyl, hydroxypropyl and hydroxybutyl.

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less.

"Sulphamoyl" is $NH_2$—$S(O)_2$—; "N-(alkyl)sulphamoyl" is RNH—$S(O)_2$—; and "N,N-(alkyl)$_2$ sulphamoyl" is $R_2N$—$S(O)_2$—, where the R groups are alkyl as defined herein and are the same or different. In various embodiments, R is a $C_1$-$C_{10}$ alkyl group or a $C_1$-$C_6$ alkyl group.

"Pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically-acceptable carrier" refers to a diluent, adjuvant, excipient, or carrier, or other ingredient which is pharmaceutically-acceptable and with which a compound of the invention is administered.

"Pharmaceutically-acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-enel-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

"Therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants.

In one embodiment, the invention provides a compound of Formula (I) or a pharmaceutically acceptable salt thereof:

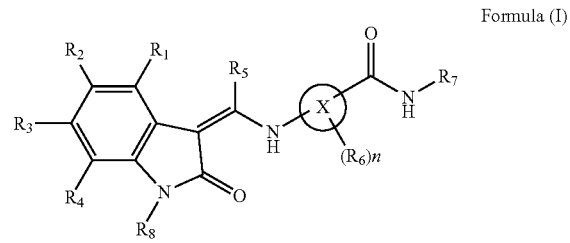

Formula (I)

wherein $R^1$, $R^2$, $R^3$, $R^4$, $R^5$, $R^6$, $R^7$, $R^8$ and X are as defined in various embodiments above.

In particular embodiments where X is phenyl or thiophene, compounds are selected from those of Formula (I-a) and Formula (I-b), with substituents defined as in Formula (I):

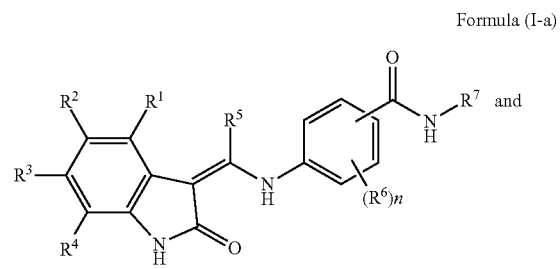

Formula (I-a)

and

Formula (I-b)

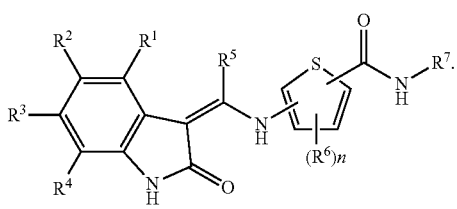

In various embodiments, compounds of Formula (I), (I-a), or (I-b) are characterized by the following:

$R^1$, $R^2$, $R^3$, and $R^4$ are independently selected from the group consisting of H, halo, nitro, cyano, hydroxy, hydroxyalkyl, haloalkyl, haloalkoxy, amino, azido, carboxyl, carbamoyl, mercapto, sulphamoyl, alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N-($C_{1-6}$ alkyl)amino, N-(heterocyclyl $C_{1-10}$ alkyl)amino, N,N—($C_{1-6}$ alkyl)$_2$amino, $C_{1-6}$ alkanoylamino, N-($C_{1-6}$ alkyl)carbamoyl, N,N-($C_{1-6}$ alkyl)$_2$carbamoyl, $C_{1-6}$ alkyl-S(O)$_a$ wherein a is 0, 1 or 2, $C_{1-6}$ alkoxycarbonyl, $NH_2$—S(O)$_2$NH—, N-($C_{1-6}$ alkyl)sulphamoyl, N,N-($C_{1-6}$ alkyl)$_2$sulphamoyl, aryl, aryloxy, arylthio, heteroaryl, heteroaryloxy, cycloalkyl, cycloalkyloxy, heterocyclyl, heterocyclyl(C=O)—, heterocyclyloxy and heterocyclylthio, wherein each of $R^1$, $R^2$, $R^3$, and $R^4$ is optionally substituted by one or more A where such an optional substitution is chemically feasible;

$R^5$ is selected from the group consisting of H, halo, haloalkyl, amino, $C_{1-6}$ alkyl, N-($C_{1-6}$ alkyl)amino and N,N-($C_{1-6}$ alkyl)$_2$ amino wherein $R^5$ is optionally substituted by one or more B;

$R^6$ is H, halo, nitro, cyano, trifluoromethyl, trifluoromethoxy, amino, carboxyl, carbamoyl, sulphamoyl, $C_{1-3}$ alkyl, $C_{2-3}$ alkenyl, $C_{2-3}$ alkynyl, $C_{1-3}$ alkoxy, $C_{1-3}$ alkanoyl, N-($C_{1-3}$ alkyl)amino, N,N-($C_{1-2}$ alkyl)$_2$ amino, $C_{1-3}$ alkanoylamino, N-($C_{1-3}$ alkyl)carbamoyl, N,N-($C_{1-2}$ alkyl)$_2$ carbamoyl, $C_{1-3}$ alkyl-S(O)$_a$ wherein a is 0, 1 or 2, $NH_2$—S(O)$_2$NH—, N-($C_{1-3}$ alkyl)sulphamoyl or N,N-($C_{1-3}$ alkyl)$_2$sulphamoyl;

$R^7$ is hydroxy, aryl or heteroaryl, wherein aryl or heteroaryl are substituted with —$NH_2$ or —OH and aryl or heteroaryl is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl;

$R^8$ is H or alkyl; and

A and B are independently selected from halo, nitro, cyano, hydroxy, oxo, hydroxyalkyl, haloalkyl, haloalkoxy, amino, azido, carboxyl, carbamoyl, mercapto, sulphamoyl, $C_{1-6}$ alkyl, $C_{2-6}$ alkenyl, $C_{2-6}$ alkynyl, $C_{1-6}$ alkoxy, $C_{1-6}$ alkanoyl, $C_{1-6}$ alkanoyloxy, N-($C_{1-6}$ alkyl)amino, N-(heterocyclyl $C_{1-10}$ alkyl)amino, N,N-($C_{1-4}$ alkyl)$_2$amino, $C_{1-6}$ alkanoylamino, N-($C_{1-6}$ alkyl)carbamoyl, N,N-($C_{1-6}$ alkyl)$_2$carbamoyl, $C_{1-6}$ alkyl-S(O)$_a$ wherein a is 0, 1 or 2, $C_{1-6}$ alkoxycarbonyl, N-($C_{1-6}$ alkyl)sulphamoyl, N,N-($C_{1-6}$ alkyl)$_2$sulphamoyl, $H_2NS(O)_2NH$—, N-($C_{1-6}$ alkyl)NHS(O)$_2$NH—, N,N-($C_{1-6}$ alkyl)$_2$NS(O)$_2$NH—, aryl, aryloxy, arylthio, heteroaryl, heteroaryloxy, cycloalkyl, cycloalkyloxy, heterocyclyl, heterocyclyl(C=O)—, heterocyclyloxy and heterocyclylthio.

In an embodiment of the compounds, one or more (including all) of the substituents $R^1$, $R^2$, $R^3$, $R^4$, $R^5$, $R^6$ and $R^7$ are further limited as follows:

$R^1$, $R^2$, $R^3$ and $R^4$ are independently selected from H, chloro, fluoro, bromo, methyl, ethyl, propyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminomethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy; in an embodiment, at least two of $R^1$, $R^2$, $R^3$ and $R^4$ are H; in an embodiment only $R^2$ is non-hydrogen and is selected from carboxyl, alkoxycarbonyl, (N,N-dialkylamino)alkylaminocarbonyl, N,N-dialkylaminocarbonyl, cyano, alkanoyl, hydroxyalkyl, heterocyclyl, alkylsulfonyl, and heterocycylsulfonyl.

$R^5$ is H, haloalkyl, amino or $C_{1-10}$ alkyl;

$R^6$ is independently fluoro, chloro, bromo, or methyl and n is 0, 1 or 2; and $R^7$ is hydroxy, aryl or heteroaryl, wherein aryl or heteroaryl are substituted with —$NH_2$ or —OH at a ring position adjacent to attachment of the —CONH-moiety, and $R^7$ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

In particular embodiments, $R^7$ is hydroxy,

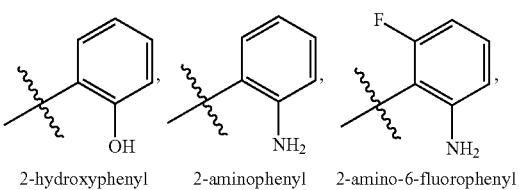

2-hydroxyphenyl    2-aminophenyl    2-amino-6-fluorophenyl

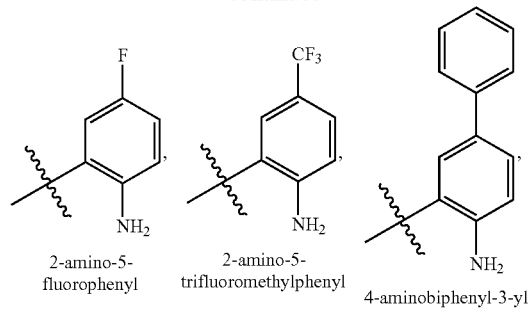

2-amino-5-fluorophenyl 2-amino-5-trifluoromethylphenyl 4-aminobiphenyl-3-yl

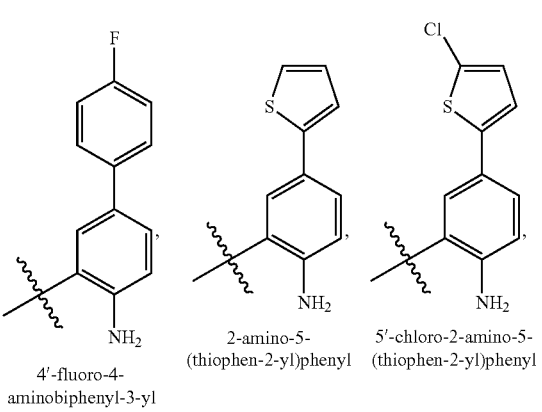

4'-fluoro-4-aminobiphenyl-3-yl 2-amino-5-(thiophen-2-yl)phenyl

5'-chloro-2-amino-5-(thiophen-2-yl)phenyl

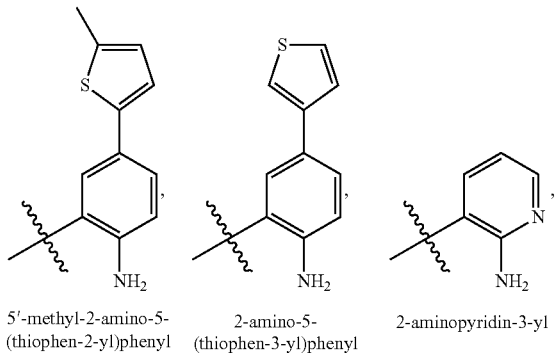

5'-methyl-2-amino-5-(thiophen-2-yl)phenyl 2-amino-5-(thiophen-3-yl)phenyl 2-aminopyridin-3-yl

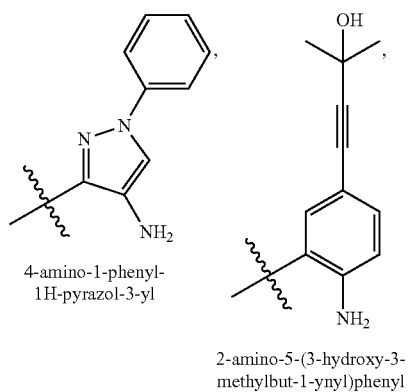

4-amino-1-phenyl-1H-pyrazol-3-yl 2-amino-5-(3-hydroxy-3-methylbut-1-ynyl)phenyl

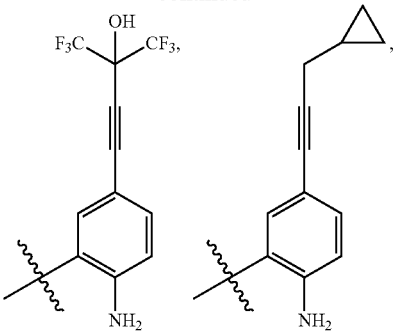

2-amino-5-(4,4,4-trifluoro-3-hydroxy-3-(trifluoromethyl)but-1-ynyl)phenyl 2-amino-5-(3-cyclopropylprop-1-ynyl)phenyl

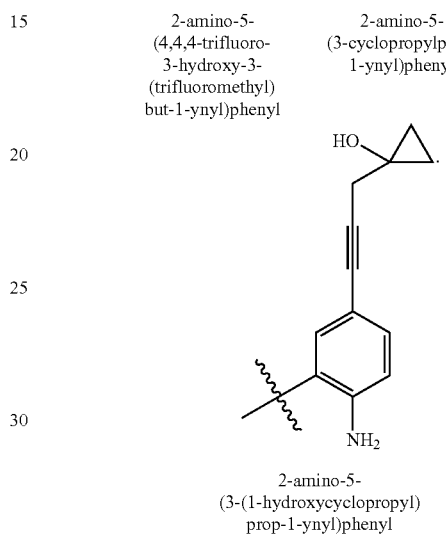

2-amino-5-(3-(1-hydroxycyclopropyl)prop-1-ynyl)phenyl

In various embodiments, the NH linker and —CONHR$^7$ moiety are disposed about the phenyl ring of Formula (I-a) in either a 1,3-(meta) or a 1,4-(para) configuration. R$^6$ can be attached to any ring position of the phenyl ring that is not occupied by the NH linker and —CONHR$^7$ moiety; such disposition of the NH linker and —CONHR$^7$ includes 1,2-(ortho), 1,3-(meta) and 1,4-(para) configurations wherein the NH linker is at position 1. In the Tables that follow, ortho-, meta- and para-configurations of R$^6$ mean attachment to positions 2, 3, and 4 of the phenyl ring as shown in Formula (I-a). Where R$^6$ is an ortho-substitution (i.e., position 2), meta-CONHR$^7$ moiety is intended to be at position 5.

Non-limiting examples of compounds of Formula (I-a) include the compounds listed in Table 1 and their pharmaceutically acceptable salts. In Table 1 and Structure (A), n of Formula (I-a) is 0 or 1. When n is 0, this is indicated by "H" in the R$^6$ column, when n is 1, Table 1 lists the non-hydrogen substituent R$^6$ as well as its position on the phenyl ring.

(A)

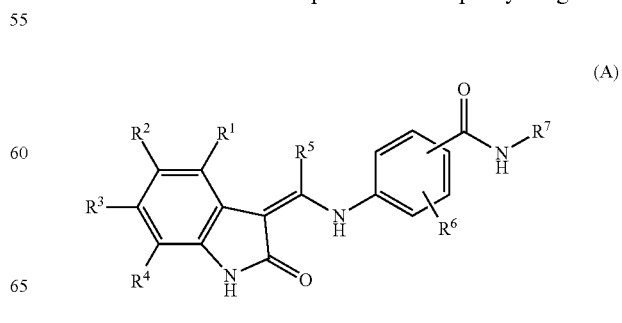

TABLE 1

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-01 | H | H | H | H | H | H | para | —OH |
| a-02 | H | H | H | H | H | H | meta | —OH |
| a-03 | H | H | H | H | H | H | para | 2-aminophenyl |
| a-04 | H | H | H | H | H | H | meta | 2-aminophenyl |
| a-05 | H | H | H | H | —CH₃ | H | para | —OH |
| a-06 | H | H | H | H | —CH₃ | H | meta | —OH |
| a-07 | H | H | H | H | —CH₃ | H | para | 2-aminophenyl |
| a-08 | H | H | H | H | —CH₃ | H | meta | 2-aminophenyl |
| a-09 | —Cl | H | H | H | H | H | para | —OH |
| a-10 | H | —Cl | H | H | H | H | para | —OH |
| a-11 | H | H | —Cl | H | H | H | para | —OH |
| a-12 | H | H | H | —Cl | H | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-13 | —Cl | H | H | H | H | H | para | 2-aminophenyl |
| a-14 | H | —Cl | H | H | H | H | para | 2-aminophenyl |
| a-15 | H | H | —Cl | H | H | H | para | 2-aminophenyl |
| a-16 | H | H | H | —Cl | H | H | para | 2-aminophenyl |
| a-17 | —CF₃ | H | H | H | H | H | para | —OH |
| a-18 | H | —CF₃ | H | H | H | H | para | —OH |
| a-19 | H | H | —CF₃ | H | H | H | para | —OH |
| a-20 | H | H | H | —CF₃ | H | H | para | —OH |
| a-21 | —CF₃ | H | H | H | H | H | para | 2-aminophenyl |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-22 | H | —CF$_3$ | H | H | H | H | para | 2-aminophenyl |
| a-23 | H | H | —CF$_3$ | H | H | H | para | 2-aminophenyl |
| a-24 | H | H | H | —CF$_3$ | H | H | para | 2-aminophenyl |
| a-25 | —OH | H | H | H | H | H | para | —OH |
| a-26 | H | —OH | H | H | H | H | para | —OH |
| a-27 | H | H | —OH | H | H | H | para | —OH |
| a-28 | H | H | H | —OH | H | H | para | —OH |
| a-29 | —OH | H | H | H | H | H | para | 2-aminophenyl |
| a-30 | H | —OH | H | H | H | H | para | 2-aminophenyl |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-31 | H | H | —OH | H | H | H | para | 2-aminophenyl |
| a-32 | H | H | H | —OH | H | H | para | 2-aminophenyl |
| a-33 | H | (CH₃)₂N-CH< | H | H | H | H | para | —OH |
| a-34 | H | H | H | H | H | H | para | —OH |
| a-35 | H | H | (CH₃)₂N-CH< | H | H | H | para | —OH |
| a-36 | H | H | H | (CH₃)₂N-CH< | H | H | para | —OH |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-37 |  | H | H | H | H | H | para | 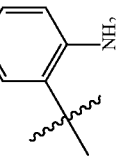 |
| a-38 | H | 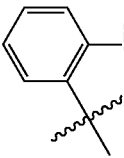 | H | H | H | H | para | 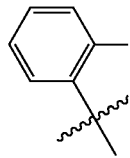 |
| a-39 | H | H |  | H | H | H | para |  |
| a-40 | H | H | H |  | H | H | para |  |
| a-41 |  | H | H | H | H | H | para | —OH |
| a-42 | H |  | H | H | H | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-43 | H | H | ![pyrrolidine-CH] | H | H | H | para | —OH |
| a-44 | H | H | H | ![pyrrolidine-CH] | H | H | para | —OH |
| a-45 | ![pyrrolidine-CH] | H | H | H | H | H | para | ![2-aminophenyl] |
| a-46 | H | ![pyrrolidine-CH] | H | H | H | H | para | ![2-aminophenyl] |
| a-47 | H | H | ![pyrrolidine-CH] | H | H | H | para | ![2-aminophenyl] |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-48 | H | H | H | 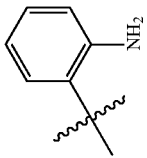 | H | H | para | 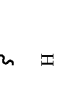 |
| a-49 | H | H | H | H | H | H | para | —OH |
| a-50 | H | 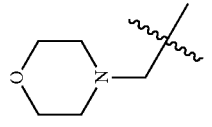 | H | H | H | H | para | —OH |
| a-51 | H | H | 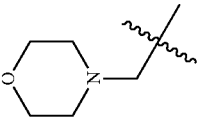 | H | H | H | para | —OH |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-52 | H | H | H | 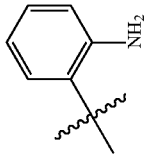 | H | H | para | —OH |
| a-53 | 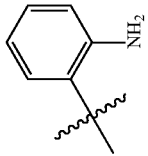 | H | H | H | H | H | para | 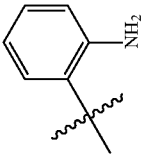 |
| a-54 | H | 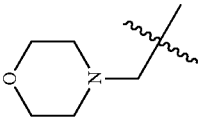 | H | H | H | H | para |  |
| a-55 | H | H |  | H | H | H | para |  |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-56 | oxetanyl-O- | H | H | H | H | H | para | 2-aminophenyl |
| a-57 | H | H | H | morpholinomethyl | H | H | para | 2-aminophenyl |
| a-58 | H | oxetanyl-O- | H | H | H | H | para | 2-aminophenyl |
| a-59 | H | H | oxetanyl-O- | H | H | H | para | 2-aminophenyl |
| a-60 | H | H | H | oxetanyl-O- | H | H | para | 2-aminophenyl |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-61 | imidazol-1-ylmethyl | H | H | H | H | H | para | 2-aminophenyl |
| a-62 | H | imidazol-1-ylmethyl | H | H | H | H | para | 2-aminophenyl |
| a-63 | H | H | imidazol-1-ylmethyl | H | H | H | para | 2-aminophenyl |
| a-64 | H | H | H | imidazol-1-ylmethyl | H | H | para | 2-aminophenyl |
| a-65 | CF₃CH₂NH-CH₂- | H | H | H | H | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-66 | H | ![CF₃-CH₂-NH-] | H | H | H | H | para | —OH |
| a-67 | H | H | ![CF₃-CH₂-NH-] | H | H | H | para | —OH |
| a-68 | H | H | H | ![CF₃-CH₂-NH-] | H | H | para | —OH |
| a-69 | ![MeO-CH₂CH₂-N(CH₃)-] | H | H | H | H | H | para | ![2-aminophenyl] |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-70 | H | CH₃OCH₂CH₂N(CH₃)– | H | H | H | H | para | 2-aminophenyl |
| a-71 | H | H | CH₃OCH₂CH₂N(CH₃)– | H | H | H | para | 2-aminophenyl |
| a-72 | H | H | H | CH₃OCH₂CH₂N(CH₃)– | H | H | para | 2-aminophenyl |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-73 | CF₃-CH₂-NH- | H | H | H | H | H | para | 2-aminophenyl |
| a-74 | H | CF₃-CH₂-NH- | H | H | H | H | para | 2-aminophenyl |
| a-75 | H | H | CF₃-CH₂-NH- | H | H | H | para | 2-aminophenyl |
| a-76 | H | H | H | CF₃-CH₂-NH- | H | H | para | 2-aminophenyl |
| a-77 | cyclopropylmethyl | H | H | H | H | H | para | 2-aminophenyl |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-78 | H | —CH₂-cyclopropyl | H | H | H | H | para | 2-aminophenyl |
| a-79 | H | H | —CH₂-cyclopropyl | H | H | H | para | 2-aminophenyl |
| a-80 | H | H | H | —CH₂-cyclopropyl | H | H | para | 2-aminophenyl |
| a-81 | cyclopropyl | H | H | H | H | H | para | 2-aminophenyl |
| a-82 | H | cyclopropyl | H | H | H | H | para | 2-aminophenyl |
| a-83 | H | H | cyclopropyl | H | H | H | para | 2-aminophenyl |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-84 | H | H | H |  | H | H | para |  |
| a-85 |  | H | H | H | H | H | para |  |
| a-86 | H |  | H | H | H | H | para |  |
| a-87 | H | H |  | H | H | H | para |  |
| a-88 | H | H | H |  | H | H | para | (2-aminophenyl) |
Note: a-88 R⁷ shown as 2-aminophenyl group.

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-89 | cyclopropyl-CH(CH₃)-O- | H | H | H | H | H | para | 2-aminophenyl |
| a-90 | H | cyclopropyl-CH(CH₃)-O- | H | H | H | H | para | 2-aminophenyl |
| a-91 | H | H | cyclopropyl-CH(CH₃)-O- | H | H | H | para | 2-aminophenyl |
| a-92 | H | H | H | cyclopropyl-CH(CH₃)-O- | H | H | para | 2-aminophenyl |
| a-93 | cyclopropyl-CH₂-NH-C(CH₃)₂- | H | H | H | H | H | para | 2-aminophenyl |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-94 | H | 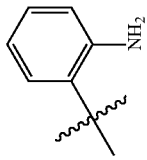 | H | H | H | H | para | 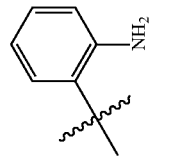 |
| a-95 | H | H | 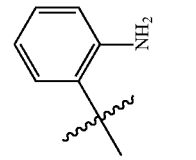 | H | H | H | para | 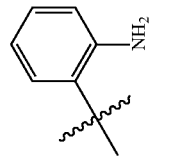 |
| a-96 | H | H | H | 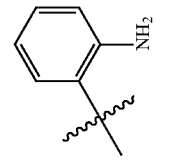 | H | H | para | 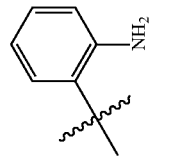 |
| a-97 |  | H | H | H | H | H | para | 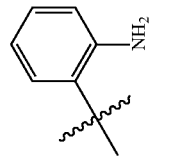 |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-98 | H |  | H | H | H | H | para |  |
| a-99 | H | H |  | H | H | H | para |  |
| a-100 | H | H | H |  | H | H | para | 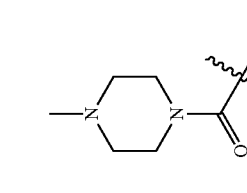 |
| a-101 | 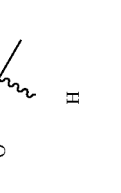 | H | H | H | H | H | para |  |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-102 | H | isoindolinyl | H | H | H | H | para | 2-aminophenyl |
| a-103 | H | H | isoindolinyl | H | H | H | para | 2-aminophenyl |
| a-104 | H | H | H | isoindolinyl | H | H | para | 2-aminophenyl |
| a-105 | —F | H | H | H | H | H | para | —OH |
| a-106 | —F | H | H | H | H | H | para | 2-aminophenyl |
| a-107 | H | H | —Br | H | H | H | para | —OH |
| a-108 | H | H | —Br | H | H | H | para | 2-aminophenyl |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-109 | H | methoxyethyl-NH-C(O)-C(CH₃)₂- | H | H | H | H | para | —OH |
| a-110 | H | methoxyethyl-NH-C(O)-C(CH₃)₂- | H | H | H | H | para | 2-aminophenyl |
| a-111 | H | H | methoxyethyl-NH-C(O)-C(CH₃)₂- | H | H | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-112 | H | H | ![R3: methoxyethyl amide of isobutyryl] | H | H | H | para | ![2-aminophenyl] |
| a-113 | H | ![morpholinoethyl amide of isobutyryl] | H | H | H | H | para | —OH |
| a-114 | H | ![morpholinoethyl amide of isobutyryl] | H | H | H | H | para | ![2-aminophenyl] |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-115 | H | H |  | H | H | H | para | —OH |
| a-116 | H | H |  | H | H | H | para |  |
| a-117 | H |  | H | H | H | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-118 | H | 4-methylpiperazine-1-carbonyl | H | H | H | H | para | 2-aminophenyl |
| a-119 | H | H | 4-methylpiperazine-1-carbonyl | H | H | H | para | —OH |
| a-120 | H | H | 4-methylpiperazine-1-carbonyl | H | H | H | para | 2-aminophenyl |
| a-121 | H | 2-morpholinoethoxy | H | H | H | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-122 | H | morpholine-N-CH₂CH₂-O-* | H | H | H | H | para | 2-aminophenyl-CH₂-* |
| a-123 | H | (CH₃)₂N-CH₂CH₂-O-* | H | H | H | H | para | —OH |
| a-124 | H | (CH₃)₂N-CH₂CH₂-O-* | H | H | H | H | para | 2-aminophenyl-CH₂-* |
| a-125 | H | CH₃-O-CH₂CH₂-O-* | H | H | H | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-126 | H | methoxyethoxy | H | H | H | H | para | 2-aminophenyl |
| a-127 | H | H | methoxyethoxy | H | H | H | para | —OH |
| a-128 | H | H | methoxyethoxy | H | H | H | para | 2-aminophenyl |
| a-129 | H | (dimethylamino)ethylamino | H | H | H | H | para | —OH |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-130 | H | 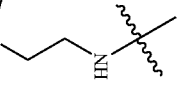 | H | H | H | H | para | 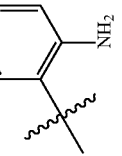 |
| a-131 | H | H | —OCH₃ | H | H | H | para | —OH |
| a-132 | H | H | —OCH₃ | H | H | H | para | —OH |
| a-133 | H | —OCH₃ | H | H | H | H | para | 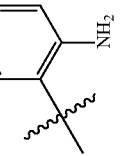 |
| a-134 | H | —OCH₃ | H | H | H | H | para | —OH |
| a-135 | H | 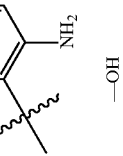 | H | H | H | H | para | 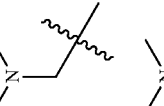 |
| a-136 | H | 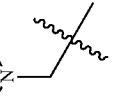 | H | H | H | H | para | —OH |
| a-137 | H | —CN | H | H | H | H | para | —OH |

TABLE 1-continued

Compounds of Structure (A)

| Compound No | $R^1$ | $R^2$ | $R^3$ | $R^4$ | $R^5$ | $R^6$ | —CONHR$^7$ attachment | $R^7$ |
|---|---|---|---|---|---|---|---|---|
| a-138 | H | —CN | H | H | H | H | para | 2-aminophenyl (methyl-linked) |
| a-139 | H | —CN | H | H | —CH$_3$ | H | para | —OH |
| a-140 | H | —CN | H | H | —CH$_3$ | H | para | 2-aminophenyl (methyl-linked) |
| a-141 | H | —C(CH$_3$)(CO$_2$CH$_3$)— | H | H | H | H | para | —OH |
| a-142 | H | —C(CH$_3$)(CO$_2$CH$_3$)— | H | H | H | H | para | 2-aminophenyl (methyl-linked) |
| a-143 | H | —C(CH$_3$)(CO$_2$CH$_3$)— | H | H | —CH$_3$ | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-144 | H | methyl 2-methylpropanoate ester group | H | H | —CH₃ | H | para | 2-aminophenyl |
| a-145 | H | —COOH | H | H | H | H | para | —OH |
| a-146 | H | —COOH | H | H | H | H | para | 2-aminophenyl |
| a-147 | H | —COOH | H | H | —CH₃ | H | para | —OH |
| a-148 | H | —COOH | H | H | —CH₃ | H | para | 2-aminophenyl |
| a-149 | H | N,N-dimethylaminoethyl amide of 2-methylpropanoyl | H | H | H | H | para | —OH |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-150 | H | 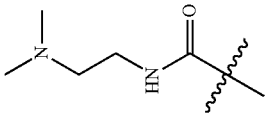 | H | H | H | H | para | 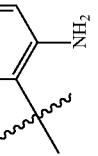 |
| a-151 | H | 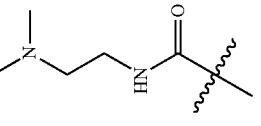 | H | H | —CH₃ | H | para | —OH |
| a-152 | H | 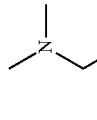 | H | H | —CH₃ | H | para | 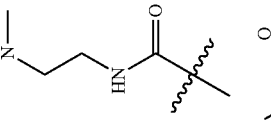 |
| a-153 | H | 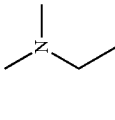 | H | H | H | H | para | —OH |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-154 | H |  | H | H | H | H | para |  |
| a-155 | H |  | H | H | —CH₃ | H | para | —OH |
| a-156 | H |  | H | H | —CH₃ | H | para | 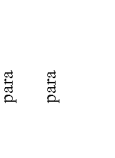 |
| a-157 | H | —C(O)CH₃ | H | H | H | H | para | —OH |
| a-158 | H | —C(O)CH₃ | H | H | H | H | para | 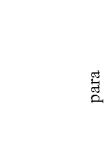 |
| a-159 | H | —C(O)CH₃ | H | H | —CH₃ | H | para | —OH |
| a-160 | H | —C(O)CH₃ | H | H | —CH₃ | H | para |  |
| a-161 | H |  | H | H | H | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-162 | H | 2-hydroxypropan-2-yl | H | H | H | H | para | 2-aminophenyl |
| a-163 | H | 2-hydroxypropan-2-yl | H | H | —CH₃ | H | para | —OH |
| a-164 | H | 2-hydroxypropan-2-yl | H | H | —CH₃ | H | para | —OH |
| a-165 | H | 3-methyl-2-oxobutan-2-yl | H | H | H | H | para | 2-aminophenyl |
| a-166 | H | 3-methyl-2-oxobutan-2-yl | H | H | H | H | para | —OH |
| a-167 | H | 3-methyl-2-oxobutan-2-yl | H | H | —CH₃ | H | para | —OH |

TABLE 1-continued
Compounds of Structure (A)
| Compound No | $R^1$ | $R^2$ | $R^3$ | $R^4$ | $R^5$ | $R^6$ | —$CONHR^7$ attachment | $R^7$ |
|---|---|---|---|---|---|---|---|---|
| a-168 | H |  | H | H | —$CH_3$ | H | para | 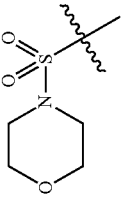 |
| a-169 | H | 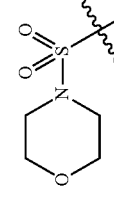 | H | H | H | H | para | —OH |
| a-170 | H | 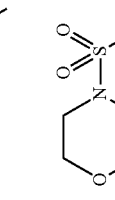 | H | H | H | H | para | 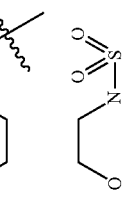 |
| a-171 | H | 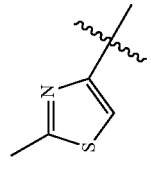 | H | H | —$CH_3$ | H | para | —OH |
| a-172 | H | | H | H | —$CH_3$ | H | para | |
| a-173 | H | | H | H | H | H | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-174 | H | 2-methylthiazol-4-yl | H | H | H | H | para | 2-aminophenyl |
| a-175 | H | 2-methylthiazol-4-yl | H | H | —CH₃ | H | para | —OH |
| a-176 | H | 2-methylthiazol-4-yl | H | H | —CH₃ | H | para | 2-aminophenyl |
| a-177 | H | CH₃S(O)₂— | H | H | H | H | para | —OH |
| a-178 | H | CH₃S(O)₂— | H | H | H | H | para | 2-aminophenyl |
| a-179 | H | CH₃S(O)₂— | H | H | —CH₃ | H | para | —OH |
| a-180 | H | CH₃S(O)₂— | H | H | —CH₃ | H | para | 2-aminophenyl |

TABLE 1-continued

Compounds of Structure (A)

| Compound No | $R^1$ | $R^2$ | $R^3$ | $R^4$ | $R^5$ | $R^6$ | —CONHR$^7$ attachment | $R^7$ |
|---|---|---|---|---|---|---|---|---|
| a-181 | H | —C(O)OCH₃ (α-methyl) | H | H | —CH₃ | ortho —F | para | —OH |
| a-182 | H | —C(O)OCH₃ (α-methyl) | H | H | —CH₃ | ortho —F | para | 2-aminophenyl |
| a-183 | H | —CN | H | H | —CH₃ | ortho —F | para | —OH |
| a-184 | H | —CN | H | H | —CH₃ | ortho —F | para | 2-aminophenyl |
| a-185 | H | —C(O)CH₃ | H | H | —CH₃ | ortho —F | para | —OH |
| a-186 | H | —C(O)CH₃ | H | H | —CH₃ | ortho —F | para | 2-aminophenyl |
| a-187 | H | —C(O)CH(CH₃)₂ (α-methyl) | H | H | —CH₃ | ortho —F | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-188 | H | ![acyl isopropyl ketone group] | H | H | —CH₃ | ortho —F | para | 2-aminophenyl |
| a-189 | H | H | H | H | —CH₂OCH₃ | H | para | —OH |
| a-190 | H | H | H | H | —CH₂OCH₃ | H | para | 2-aminophenyl |
| a-191 | H | —CF₃ | H | H | —CH₃ | H | para | —OH |
| a-192 | H | —CF₃ | H | H | —CH₃ | H | para | 2-aminophenyl |
| a-193 | H | —OCF₃ | H | H | —CH₃ | H | para | —OH |
| a-194 | H | —OCF₃ | H | H | —CH₃ | H | para | 2-aminophenyl |
| a-195 | (fused thiazolo-indolinone structure) | | | | | | para | —OH |

TABLE 1-continued

Compounds of Structure (A)

| Compound No | R¹ | R² | R³ | R⁴ | R⁵ | R⁶ | —CONHR⁷ attachment | R⁷ |
|---|---|---|---|---|---|---|---|---|
| a-196 | | | H | H | —CH₃ | H | para | 2-aminophenyl |
| a-197 | | | H | H | —CH₃ | H | para | —OH |
| a-198 | | | H | H | —CH₃ | H | para | 2-aminophenyl |

TABLE 1-continued
Compounds of Structure (A)
| Compound No | R¹ | R² | R³ | R⁴ | R⁵ | R⁶ | —CONHR⁷ attachment | R⁷ |
|---|---|---|---|---|---|---|---|---|
| a-199 | H | H | H | H | 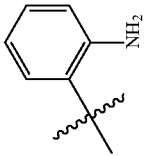 | H | para | 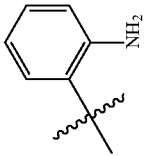 |
| a-200 | H | H | H | H | 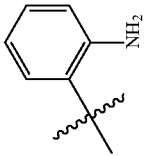 | H | meta | 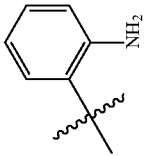 |
*In a-195, a-196, a-197 and a-198, R¹ and R² form a heterocyclic moiety. To illustrate this, the resulting fused oxindole moiety is shown in the R¹ and R² columns.

Non-limiting examples of compounds of Formula (I-b) (where the ring X is a thiophene) include the compounds and pharmaceutically acceptable salts thereof shown in Table 2 below. Table 2 discloses compounds of Formula (I-b) that in one embodiment have a 2,5-configuration on the thiophene and in another have a 2,4-configuration on the thiophene. To illustrate, the row labeled as "reference No. b-01" discloses two thiophene HDAC compounds and their pharmaceutically acceptable salts. The first compound contains the $R^1$-$R^7$ substituents of the b-01 row on a compound of Formula (I-b) where the —NH— and the —C(O)NHR$^7$ are disposed about the thiophene ring in a 2,5-configuration, with the S atom taken as position 1. The second compound (and salts) embraced by Reference No. b-01 has the same substituents $R^1$-$R^7$, but the —NH— and the —C(O)NHR$^7$ are disposed about the thiophene ring in a 2,4-configuration.

In the compounds of Structure (B) shown in Table 2, n=0 or n=1. When n=0, by convention this is indicated by a listing of "H" under the $R^6$ column. When n=1, the substituent listed in the $R^6$ column is attached to one of the two "free" positions on the thiophene ring not occupied by the —NH— or —C(O)NHR$^7$ groups. When the Reference No. discloses a 2,5-substituted thiophene, the substituent $R^6$ is on the 3-position in a first embodiment and on the 4-position in a second embodiment. Similarly, when the Reference No. discloses a 2,4-substituted thiophene, the substituent $R^6$ is on the 3-position in a first embodiment and on the 5-position in a second embodiment. This is indicated in the Table (Reference No. b-181 through b-196) by a parenthetical mention of the particular thiophene configuration below the reference no. Thus to illustrate, each of Reference No. b-181 (hydroxamate) and b-182 (arylamide) embraces both the 3-fluoro-2,5-thiophendiyl and the 4-fluoro-2,5-thiophendiyl species of the respective compound, while each of b-183 and b-184 embraces the 3-fluoro-2,4-thiophendiyl and 5-fluoro-2,4-thiophendiyl species of the respective hydroxamate and arylamide.

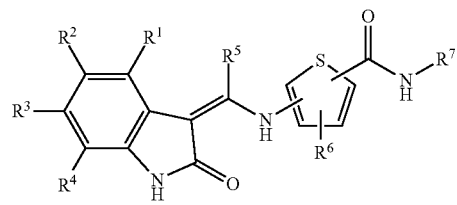

(B)

TABLE 2

Compounds of Structure (B)

| Reference No. | R¹ | R² | R³ | R⁴ | R⁵ | R⁶ | R⁷ |
|---|---|---|---|---|---|---|---|
| b-01 | H | H | H | H | H | H | —OH |
| b-02 | H | H | H | H | H | H | —OH |
| b-03 | H | H | H | H | H | H | 2-aminophenyl (with CH<) |
| b-04 | H | H | H | H | H | H | 2-aminophenyl (with CH<) |
| b-05 | H | H | H | H | —CH₃ | H | —OH |
| b-06 | H | H | H | H | —CH₃ | H | —OH |
| b-07 | H | H | H | H | —CH₃ | H | 2-aminophenyl (with CH<) |
| b-08 | H | H | H | H | —CH₃ | H | 2-aminophenyl (with CH<) |
| b-09 | —Cl | H | H | H | H | H | —OH |
| b-10 | H | —Cl | H | H | H | H | —OH |
| b-11 | H | H | —Cl | H | H | H | —OH |
| b-12 | H | H | H | —Cl | H | H | —OH |

TABLE 2-continued

Compounds of Structure (B)

| Reference No. | $R^1$ | $R^2$ | $R^3$ | $R^4$ | $R^5$ | $R^6$ | $R^7$ |
|---|---|---|---|---|---|---|---|
| b-13 | —Cl | H | H | H | H | H | 2-aminophenyl-methyl |
| b-14 | H | —Cl | H | H | H | H | 2-aminophenyl-methyl |
| b-15 | H | H | —Cl | H | H | H | 2-aminophenyl-methyl |
| b-16 | H | H | H | —Cl | H | H | 2-aminophenyl-methyl |
| b-17 | —CF$_3$ | H | H | H | H | H | —OH |
| b-18 | H | —CF$_3$ | H | H | H | H | —OH |
| b-19 | H | H | —CF$_3$ | H | H | H | —OH |
| b-20 | H | H | H | —CF$_3$ | H | H | —OH |
| b-21 | —CF$_3$ | H | H | H | H | H | 2-aminophenyl-methyl |

TABLE 2-continued

Compounds of Structure (B)

| Reference No. | R¹ | R² | R³ | R⁴ | R⁵ | R⁶ | R⁷ |
|---|---|---|---|---|---|---|---|
| b-22 | H | —CF$_3$ | H | H | H | H | 2-aminophenyl-methyl |
| b-23 | H | H | —CF$_3$ | H | H | H | 2-aminophenyl-methyl |
| b-24 | H | H | H | —CF$_3$ | H | H | 2-aminophenyl-methyl |
| b-25 | —OH | H | H | H | H | H | —OH |
| b-26 | H | —OH | H | H | H | H | —OH |
| b-27 | H | H | —OH | H | H | H | —OH |
| b-28 | H | H | H | —OH | H | H | —OH |
| b-29 | —OH | H | H | H | H | H | 2-aminophenyl-methyl |
| b-30 | H | —OH | H | H | H | H | 2-aminophenyl-methyl |

TABLE 2-continued
Compounds of Structure (B)
| Reference No. | R¹ | R² | R³ | R⁴ | R⁵ | R⁶ | R⁷ |
|---|---|---|---|---|---|---|---|
| b-31 | H | H | —OH | H | H | H | 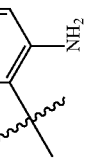 |
| b-32 | H | H | H | —OH | H | H | 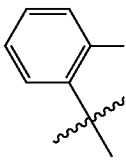 |
| b-33 | H |  | H | H | H | H | —OH |
| b-34 | H | H |  | H | H | H | —OH |
| b-35 | H | H | H | H | H | H | —OH |
| b-36 | H | H | H |  | H | H | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-37 | ![N(CH3)2-CH2-] | H | H | H | H | H | ![2-aminophenyl-CH(CH3)-] |
| b-38 | H | ![N(CH3)2-CH2-] | H | H | H | H | ![2-aminophenyl-CH(CH3)-] |
| b-39 | H | H | ![N(CH3)2-CH2-] | H | H | H | ![2-aminophenyl-CH(CH3)-] |
| b-40 | H | H | H | ![N(CH3)2-CH2-] | H | H | ![2-aminophenyl-CH(CH3)-] |
| b-41 | ![pyrrolidinyl-CH2-] | H | H | H | H | H | —OH |
| b-42 | H | ![pyrrolidinyl-CH2-] | H | H | H | H | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-43 | H | H | pyrrolidin-1-ylmethyl | H | H | H | —OH |
| b-44 | H | H | H | pyrrolidin-1-ylmethyl | H | H | —OH |
| b-45 | pyrrolidin-1-ylmethyl | H | H | H | H | H | 2-aminophenyl-methyl |
| b-46 | H | pyrrolidin-1-ylmethyl | H | H | H | H | 2-aminophenyl-methyl |
| b-47 | H | H | pyrrolidin-1-ylmethyl | H | H | H | 2-aminophenyl-methyl |

TABLE 2-continued

Compounds of Structure (B)

| Reference No. | R¹ | R² | R³ | R⁴ | R⁵ | R⁶ | R⁷ |
|---|---|---|---|---|---|---|---|
| b-48 | H | H | H | pyrrolidinyl-CH₂- | H | H | 2-aminophenyl-CH(CH₃)- |
| b-49 | morpholinyl-CH₂- | H | H | H | H | H | 2-aminophenyl-CH(CH₃)- |
| b-50 | H | morpholinyl-CH₂- | H | H | H | H | 2-aminophenyl-CH(CH₃)- |
| b-51 | H | H | morpholinyl-CH₂- | H | H | H | 2-aminophenyl-CH(CH₃)- |

TABLE 2-continued
Compounds of Structure (B)
| Reference No. | R¹ | R² | R³ | R⁴ | R⁵ | R⁶ | R⁷ |
|---|---|---|---|---|---|---|---|
| b-52 | H | H | H | 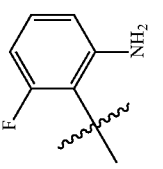 | H | H | 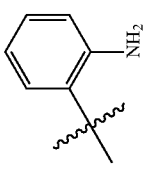 |
| b-53 |  | H | H | H | H | H | 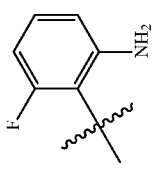 |
| b-54 | H |  | H | H | H | H | 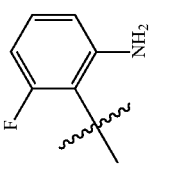 |
| b-55 | H | H | 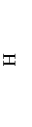 | H | H | H |  |

TABLE 2-continued

Compounds of Structure (B)

| Reference No. | R¹ | R² | R³ | R⁴ | R⁵ | R⁶ | R⁷ |
|---|---|---|---|---|---|---|---|
| b-56 | H | H | H | morpholinomethyl | H | H | 3-fluoro-2-aminophenyl |
| b-57 | oxetan-3-yloxy | H | H | H | H | H | 2-aminophenyl |
| b-58 | H | oxetan-3-yloxy | H | H | H | H | 2-aminophenyl |
| b-59 | H | H | oxetan-3-yloxy | H | H | H | 2-aminophenyl |
| b-60 | H | H | H | oxetan-3-yloxy | H | H | 2-aminophenyl |

TABLE 2-continued

Compounds of Structure (B)

| Reference No. | R¹ | R² | R³ | R⁴ | R⁵ | R⁶ | R⁷ |
|---|---|---|---|---|---|---|---|
| b-61 | imidazol-1-ylmethyl | H | H | H | H | H | 2-aminophenyl |
| b-62 | H | imidazol-1-ylmethyl | H | H | H | H | 2-aminophenyl |
| b-63 | H | H | imidazol-1-ylmethyl | H | H | H | 2-aminophenyl |
| b-64 | H | H | H | imidazol-1-ylmethyl | H | H | 2-aminophenyl |
| b-65 | CF₃CH₂NH-CH₂– | H | H | H | H | H | 2-aminophenyl |

TABLE 2-continued

Compounds of Structure (B)

| Reference No. | R¹ | R² | R³ | R⁴ | R⁵ | R⁶ | R⁷ |
|---|---|---|---|---|---|---|---|
| b-66 | H | ![CF₃-CH₂-NH-] | H | H | H | H | ![2-aminophenyl] |
| b-67 | H | H | ![CF₃-CH₂-NH-] | H | H | H | ![2-aminophenyl] |
| b-68 | H | H | H | ![CF₃-CH₂-NH-] | H | H | ![2-aminophenyl] |
| b-69 | ![MeO-CH₂CH₂-N(Me)-] | H | H | H | | H | ![2-aminophenyl] |

TABLE 2-continued

Compounds of Structure (B)

| Reference No. | R¹ | R² | R³ | R⁴ | R⁵ | R⁶ | R⁷ |
|---|---|---|---|---|---|---|---|
| b-70 | H | CH₃OCH₂CH₂N(CH₃)- | H | H | H | H | 2-aminophenyl (methyl-substituted) |
| b-71 | H | H | CH₃OCH₂CH₂N(CH₃)- | H | H | H | 2-aminophenyl (methyl-substituted) |
| b-72 | H | H | H | CH₃OCH₂CH₂N(CH₃)- | H | H | 2-aminophenyl (methyl-substituted) |

TABLE 2-continued

Compounds of Structure (B)

| Reference No. | R¹ | R² | R³ | R⁴ | R⁵ | R⁶ | R⁷ |
|---|---|---|---|---|---|---|---|
| b-73 | CF₃-NH-* | H | H | H | H | H | 3-F-2-aminophenyl |
| b-74 | H | CF₃-NH-* | H | H | H | H | 3-F-2-aminophenyl |
| b-75 | H | H | CF₃-NH-* | H | H | H | 3-F-2-aminophenyl |
| b-76 | H | H | H | CF₃-NH-* | H | H | 3-F-2-aminophenyl |
| b-77 | cyclopropyl-CH₂-* | H | H | H | H | H | 2-aminophenyl |

TABLE 2-continued
Compounds of Structure (B)
| Reference No. | $R^1$ | $R^2$ | $R^3$ | $R^4$ | $R^5$ | $R^6$ | $R^7$ |
|---|---|---|---|---|---|---|---|
| b-78 | H | 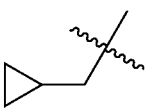 | H | H | H | H | 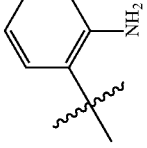 |
| b-79 | H | H |  | H | H | H | 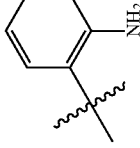 |
| b-80 | H | H | H |  | H | H | 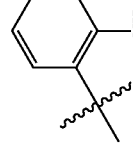 |
| b-81 |  | H | H | H | H | H | 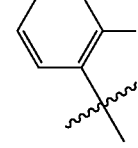 |
| b-82 | H | 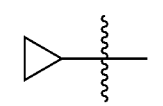 | H | H | H | H | 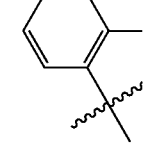 |
| b-83 | H | H |  | H | H | H | 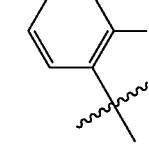 |

TABLE 2-continued

Compounds of Structure (B)

| Reference No. | R¹ | R² | R³ | R⁴ | R⁵ | R⁶ | R⁷ |
|---|---|---|---|---|---|---|---|
| b-84 | H | H | H | cyclopropyl | H | H | 2-aminophenyl |
| b-85 | cyclobutoxy | H | H | H | H | H | 2-aminophenyl |
| b-86 | H | cyclobutoxy | H | H | H | H | 2-aminophenyl |
| b-87 | H | H | cyclobutoxy | H | H | H | 2-aminophenyl |
| b-88 | H | H | H | cyclobutoxy | H | H | 2-aminophenyl |

TABLE 2-continued

Compounds of Structure (B)

| Reference No. | $R^1$ | $R^2$ | $R^3$ | $R^4$ | $R^5$ | $R^6$ | $R^7$ |
|---|---|---|---|---|---|---|---|
| b-89 | cyclopropyl-CH(CH₃)-O- | H | H | H | H | H | 2-aminophenyl-C(CH₃)- |
| b-90 | H | cyclopropyl-CH(CH₃)-O- | H | H | H | H | 2-aminophenyl-C(CH₃)- |
| b-91 | H | H | cyclopropyl-CH(CH₃)-O- | H | H | H | 2-aminophenyl-C(CH₃)- |
| b-92 | H | H | H | cyclopropyl-CH(CH₃)-O- | H | H | 2-aminophenyl-C(CH₃)- |
| b-93 | cyclopropyl-CH₂-NH-C(CH₃)- | H | H | H | H | H | 2-aminophenyl-C(CH₃)- |

TABLE 2-continued

Compounds of Structure (B)

| Reference No. | R¹ | R² | R³ | R⁴ | R⁵ | R⁶ | R⁷ |
|---|---|---|---|---|---|---|---|
| b-94 | H | cyclopropylmethylamino | H | H | H | H | 2-aminophenyl(methyl) |
| b-95 | H | H | cyclopropylmethylamino | H | H | H | 2-aminophenyl(methyl) |
| b-96 | H | H | H | cyclopropylmethylamino | H | H | 2-aminophenyl(methyl) |
| b-97 | 4-methylpiperazin-1-yl-carbonyl | H | H | H | H | H | 2-aminophenyl(methyl) |

TABLE 2-continued
Compounds of Structure (B)
| Reference No. | R¹ | R² | R³ | R⁴ | R⁵ | R⁶ | R⁷ |
|---|---|---|---|---|---|---|---|
| b-98 | H | 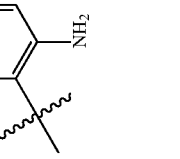 | H | H | H | H |  |
| b-99 | H | H |  | H | H | H |  |
| b-100 | H | H | H |  | H | H | 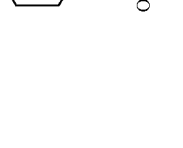 |
| b-101 | 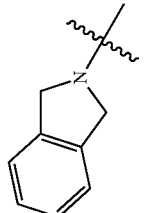 | H | H | H | H | H | (2-aminophenyl) |

TABLE 2-continued

Compounds of Structure (B)

| Reference No. | R¹ | R² | R³ | R⁴ | R⁵ | R⁶ | R⁷ |
|---|---|---|---|---|---|---|---|
| b-102 | H | isoindolinyl | H | H | H | H | 2-aminophenyl |
| b-103 | H | H | isoindolinyl | H | H | H | 2-aminophenyl |
| b-104 | H | H | H | isoindolinyl | H | H | 2-aminophenyl |
| b-105 | —F | H | H | H | H | H | 2-aminophenyl |
| b-106 | —F | H | H | H | H | H | 2-aminophenyl |
| b-107 | H | H | —Br | H | H | H | 2-aminophenyl |

TABLE 2-continued

Compounds of Structure (B)

| Reference No. | R¹ | R² | R³ | R⁴ | R⁵ | R⁶ | R⁷ |
|---|---|---|---|---|---|---|---|
| b-108 | H | H | —Br | H | H | H | 2-aminophenyl (methyl-linked) |
| b-109 | H | methoxyethyl-NH-C(O)-C(CH₃)₂- | H | H | H | H | 2-aminophenyl (methyl-linked) |
| b-110 | H | methoxyethyl-NH-C(O)-C(CH₃)₂- | H | H | H | H | 2-aminophenyl (methyl-linked) |
| b-111 | H | H | methoxyethyl-NH-C(O)-C(CH₃)₂- | H | H | H | 2-aminophenyl (methyl-linked) |

TABLE 2-continued

Compounds of Structure (B)

| Reference No. | R¹ | R² | R³ | R⁴ | R⁵ | R⁶ | R⁷ |
|---|---|---|---|---|---|---|---|
| b-112 | H | H | methoxyethyl-NH-C(O)-C(CH₃)₂- | H | H | H | 2-aminophenyl-C(CH₃)- |
| b-113 | H | morpholinoethyl-NH-C(O)-C(CH₃)₂- | H | H | H | H | 2-aminophenyl-C(CH₃)- |
| b-114 | H | morpholinoethyl-NH-C(O)-C(CH₃)₂- | H | H | H | H | 2-aminophenyl-C(CH₃)- |

TABLE 2-continued
Compounds of Structure (B)
| Reference No. | R¹ | R² | R³ | R⁴ | R⁵ | R⁶ | R⁷ |
|---|---|---|---|---|---|---|---|
| b-115 | H | H |  | H | H | H | 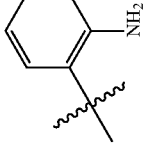 |
| b-116 | H | H | 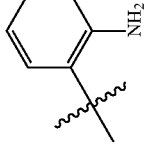 | H | H | H | 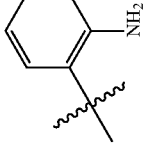 |
| b-117 | H | 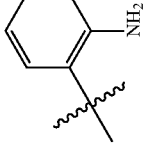 | H | H | H | H | 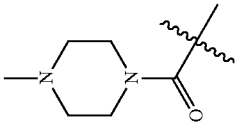 |

TABLE 2-continued

Compounds of Structure (B)

| Reference No. | R¹ | R² | R³ | R⁴ | R⁵ | R⁶ | R⁷ |
|---|---|---|---|---|---|---|---|
| b-118 | H | N-methylpiperazine carbonyl | H | H | H | H | 2-aminophenyl |
| b-119 | H | H | N-methylpiperazine carbonyl | H | H | H | 2-aminophenyl |
| b-120 | H | H | N-methylpiperazine carbonyl | H | H | H | 2-aminophenyl |
| b-121 | H | morpholinoethoxy | H | H | H | H | 2-aminophenyl |

TABLE 2-continued

Compounds of Structure (B)

| Reference No. | R¹ | R² | R³ | R⁴ | R⁵ | R⁶ | R⁷ |
|---|---|---|---|---|---|---|---|
| b-122 | H | morpholino-ethoxy | H | H | H | H | 2-aminophenyl-methyl |
| b-123 | H | dimethylamino-ethoxy | H | H | H | H | 2-aminophenyl-methyl |
| b-124 | H | dimethylamino-ethoxy | H | H | H | H | 2-aminophenyl-methyl |
| b-125 | H | methoxyethoxy | H | H | H | H | —OH |

TABLE 2-continued
Compounds of Structure (B)
| Reference No. | R¹ | R² | R³ | R⁴ | R⁵ | R⁶ | R⁷ |
|---|---|---|---|---|---|---|---|
| b-126 | H | 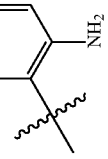 | H | H | H | H | 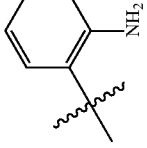 |
| b-127 | H | H | 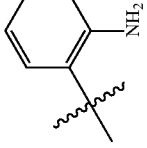 | H | H | H | —OH |
| b-128 | H | H | 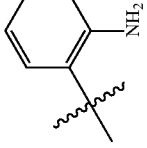 | H | H | H | 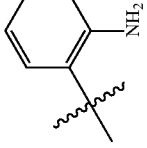 |
| b-129 | H | 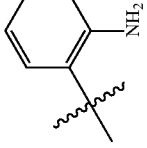 | H | H | H | H | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-130 | H | | H | H | H | H | |
| b-131 | H | H | —OCH₃ | H | H | H | —OH |
| b-132 | H | H | —OCH₃ | H | H | H | |
| b-133 | H | —OCH₃ | H | H | H | H | —OH |
| b-134 | H | —OCH₃ | H | H | H | H | |
| b-135 | H | | H | H | H | H | —OH |
| b-136 | H | | H | H | H | H | |
| b-137 | H | —CN | H | H | H | H | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-138 | H | —CN | H | H | H | H | 2-aminophenyl (attached via CH) |
| b-139 | H | —CN | H | H | —CH₃ | H | —OH |
| b-140 | H | —CN | H | H | —CH₃ | H | —OH |
| b-141 | H | methyl 2-methylpropanoate group | H | H | H | H | 2-aminophenyl (attached via CH) |
| b-142 | H | methyl 2-methylpropanoate group | H | H | H | H | 2-aminophenyl (attached via CH) |
| b-143 | H | methyl 2-methylpropanoate group | H | H | —CH₃ | H | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-144 | H | methyl 2-methylpropanoate ester group | H | H | —CH₃ | H | 2-aminophenyl (methyl-linked) |
| b-145 | H | —COOH | H | H | H | H | —OH |
| b-146 | H | —COOH | H | H | H | H | 2-aminophenyl (methyl-linked) |
| b-147 | H | —COOH | H | H | —CH₃ | H | —OH |
| b-148 | H | —COOH | H | H | —CH₃ | H | 2-aminophenyl (methyl-linked) |
| b-149 | H | N,N-dimethylaminoethyl amide of 2-methylpropanoyl | H | H | H | H | —OH |

TABLE 2-continued
Compounds of Structure (B)
| Reference No. | R¹ | R² | R³ | R⁴ | R⁵ | R⁶ | R⁷ |
|---|---|---|---|---|---|---|---|
| b-150 | H | 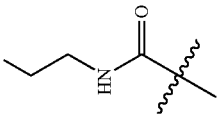 | H | H | H | H | 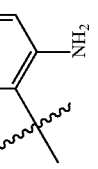 |
| b-151 | H | 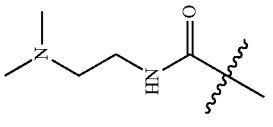 | H | H | —CH₃ | H | —OH |
| b-152 | H | 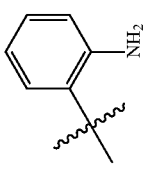 | H | H | —CH₃ | H | 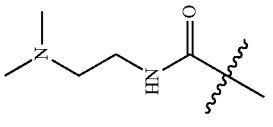 |
| b-153 | H | 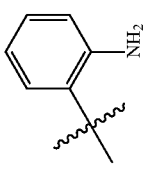 | H | H | H | H | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-154 | H | -C(O)N(CH₃)₂ (via C) | H | H | H | H | 2-aminophenyl (ortho-NH₂) |
| b-155 | H | -C(O)N(CH₃)₂ (via C) | H | H | -CH₃ | H | -OH |
| b-156 | H | -C(O)N(CH₃)₂ (via C) | H | H | -CH₃ | H | 2-aminophenyl |
| b-157 | H | -C(O)CH₃ | H | H | H | H | -OH |
| b-158 | H | -C(O)CH₃ | H | H | H | H | 2-aminophenyl |
| b-159 | H | -C(O)CH₃ | H | H | -CH₃ | H | -OH |
| b-160 | H | -C(O)CH₃ | H | H | -CH₃ | H | 2-aminophenyl |
| b-161 | H | -CH(OH)CH₃ (1-hydroxyethyl/isopropanol group) | H | H | H | H | -OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-162 | H | (HO)CH(CH₃)– (wavy) | H | H | H | H | 2-aminophenyl with methyl (wavy) |
| b-163 | H | (HO)CH(CH₃)– (wavy) | H | H | —CH₃ | H | —OH |
| b-164 | H | (HO)CH(CH₃)– (wavy) | H | H | —CH₃ | H | 2-aminophenyl with methyl (wavy) |
| b-165 | H | (CH₃)₂CHC(O)– (wavy) | H | H | H | H | —OH |
| b-166 | H | (CH₃)₂CHC(O)– (wavy) | H | H | H | H | 2-aminophenyl with methyl (wavy) |
| b-167 | H | (CH₃)₂CHC(O)– (wavy) | H | H | —CH₃ | H | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-168 | H | isobutyryl | H | H | —CH₃ | H | 2-aminophenyl |
| b-169 | H | morpholinosulfonyl | H | H | H | H | —OH |
| b-170 | H | morpholinosulfonyl | H | H | H | H | 2-aminophenyl |
| b-171 | H | morpholinosulfonyl | H | H | —CH₃ | H | —OH |
| b-172 | H | morpholinosulfonyl | H | H | —CH₃ | H | 2-aminophenyl |
| b-173 | H | 2-methylthiazol-4-yl | H | H | H | H | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-174 | H | 2-methylthiazol-4-yl | H | H | H | H | 2-aminophenyl-methyl |
| b-175 | H | 2-methylthiazol-4-yl | H | H | —CH₃ | H | —OH |
| b-176 | H | 2-methylthiazol-4-yl | H | H | —CH₃ | H | 2-aminophenyl-methyl |
| b-177 | H | CH₃S(O)₂— | H | H | H | H | 2-aminophenyl-methyl |
| b-178 | H | CH₃S(O)₂— | H | H | H | H | —OH |
| b-179 | H | CH₃S(O)₂— | H | H | —CH₃ | H | —OH |
| b-180 | H | CH₃S(O)₂— | H | H | —CH₃ | H | 2-aminophenyl-methyl |

TABLE 2-continued

Compounds of Structure (B)

| Reference No. | R¹ | R² | R³ | R⁴ | R⁵ | R⁶ | R⁷ |
|---|---|---|---|---|---|---|---|
| b-181 (2,5-thiophene) | H | methyl 2-methylpropanoate (—C(CH₃)(—)C(O)OCH₃) | H | H | —CH₃ | —F* | —OH |
| b-182 (2,5-thiophene) | H | methyl 2-methylpropanoate | H | H | —CH₃ | —F* | 2-aminophenyl (with CH₃) |
| b-183 (2,4-thiophene) | H | methyl 2-methylpropanoate | H | H | —CH₃ | —F* | —OH |
| b-184 (2,4-thiophene) | H | methyl 2-methylpropanoate | H | H | —CH₃ | —F* | 2-aminophenyl (with CH₃) |
| b-185 (2,5-thiophene) | H | —CN | H | H | —CH₃ | —F* | —OH |
| b-186 (2,5-thiophene) | H | —CN | H | H | —CH₃ | —F* | 2-aminophenyl (with CH₃) |
| b-187 (2,4-thiophene) | H | —CN | H | H | —CH₃ | —F* | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-188 (2,4-thiophene) | H | —CN | H | H | —CH₃ | —F* | 2-aminophenyl |
| b-189 (2,5-thiophene) | H | —C(O)CH₃ | H | H | —CH₃ | —F* | —OH |
| b-190 (2,4-thiophene) | H | —C(O)CH₃ | H | H | —CH₃ | —F* | 2-aminophenyl |
| b-191 (2,4-thiophene) | H | —C(O)CH₃ | H | H | —CH₃ | —F* | —OH |
| b-192 (2,4-thiophene) | H | —C(O)CH₃ | H | H | —CH₃ | —F* | 2-aminophenyl |
| b-193 (2,5-thiophene) | H | —C(O)CH(CH₃)₂ | H | H | —CH₃ | —F* | —OH |
| b-194 (2,5-thiophene) | H | —C(O)CH(CH₃)₂ | H | H | —CH₃ | —F* | 2-aminophenyl |

TABLE 2-continued
Compounds of Structure (B)
| Reference No. | R¹ | R² | R³ | R⁴ | R⁵ | R⁶ | R⁷ |
|---|---|---|---|---|---|---|---|
| b-195 (2,4-thiophene) | H | 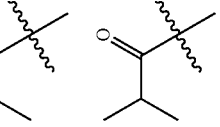 | H | H | —CH₃ | —F* | —OH |
| b-196 (2,4-thiophene) | H | 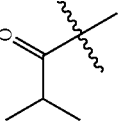 | H | H | —CH₃ | —F* | 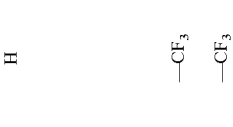 |
| b-197 | H | H | H | H | —CH₂OCH₃ | H | —OH |
| b-198 | H | H | H | H | —CH₂OCH₃ | H | 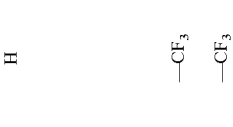 |
| b-199 | H | —CF₃ | H | H | —CH₃ | H | —OH |
| b-200 | H | —CF₃ | H | H | —CH₃ | H | 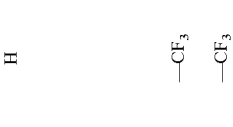 |
| b-201 | H | —OCF₃ | H | H | —CH₃ | H | —OH |
| b-202 | H | —OCF₃ | H | H | —CH₃ | H | 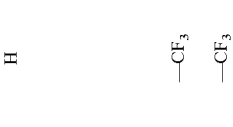 |

TABLE 2-continued

Compounds of Structure (B)

| Reference No. | R¹ | R² | R³ | R⁴ | R⁵ | R⁶ | R⁷ |
|---|---|---|---|---|---|---|---|
| b-203 | (thiazole-fused bicyclic) | (oxindole-type **) | H | H | —CH₃ | H | —OH |
| b-204 | (thiazole-fused bicyclic) | (oxindole-type **) | H | H | —CH₃ | H | (2-aminophenyl-methyl) |
| b-205 | (morpholinoethylamino-thiazole-fused bicyclic) | (oxindole-type **) | H | H | —CH₃ | H | —OH |

TABLE 2-continued

Compounds of Structure (B)

| Reference No. | R¹ | R² | R³ | R⁴ | R⁵ | R⁶ | R⁷ |
|---|---|---|---|---|---|---|---|
| b-206 | morpholinoethylamino-thiazole-fused oxindole** | H | H | H | —CH₃ | H | 2-aminophenyl (methyl-substituted) |
| b-207 | H | H | H | H | cyclopropyl | H | 2-aminophenyl |
| b-208 | H | H | H | H | cyclopropyl | H | 2-aminophenyl |

*Each of Reference Nos. b-181, b-185, b-189, and b-193 (hydroxamates) and each of b-182, b-186, b-190, and b-194 (arylamides) embraces both the 3-fluoro-2,5-thiophendiyl species of the respective compound. Each of b-183, b-187, b-191, and b-195 and each of b-184, b-188, b-192, and b-196 embraces both the 3-fluoro-2,4-thiophendiyl and 5-fluoro-2,4-thiophendiyl species of the respective hydroxamates and arylamides.
**In b-203, b-204, b-205 and b-206, R¹ and R² form a heterocyclic moiety and the oxindole moiety is shown in the R¹ and R² columns together.

In yet another embodiment, the invention provides a compound of Formula (II) or a pharmaceutically acceptable salt thereof:

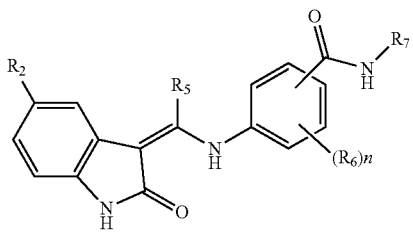

Formula (II)

wherein $R^2$ is selected from the group consisting of H, hydroxy, $C_{1-10}$ alkyl, $C_{1-10}$ alkanoyl, $C_{1-10}$ methoxy, hydroxyalkyl, halo, haloalkyl, haloalkoxy, N,N-($C_{1-10}$ alkyl)$_2$aminoalkyl, cyano, acetyl, carboxyl, methylcarboxyl, N,N-($C_{1-10}$ alkyl)$_2$aminocarbonyl, N,N-($C_{1-10}$ alkyl)$_2$aminoethyladminocarbonyl, morpholinylsulfonyl, alkylthiazolyl, $C_{1-10}$ alkyl-S(O)a wherein a is 0, 1 or 2, morpholinylmethyl and pyrrolidinylmethyl; $R^5$ is H, methyl, cyclopropyl; $R^6$ when present is halo (e.g., fluoro, bromo, or chloro) and n is 0 or 1; and $R^7$ is hydroxy or phenyl substituted with —NH$_2$ or —OH at a ring position adjacent to attachment of the —CONH-moiety, and $R^7$ is optionally substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

Examples of such compounds include:

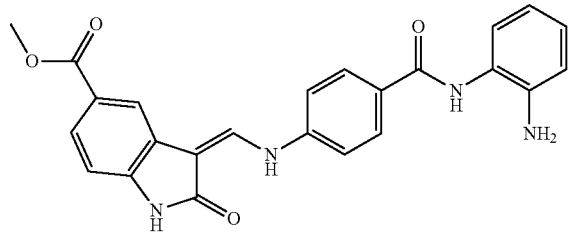

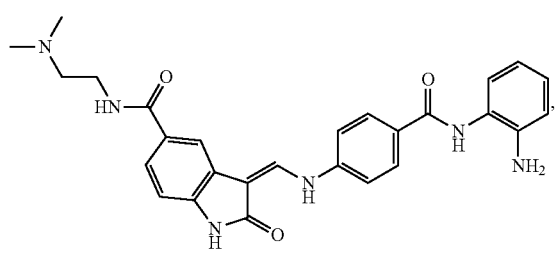

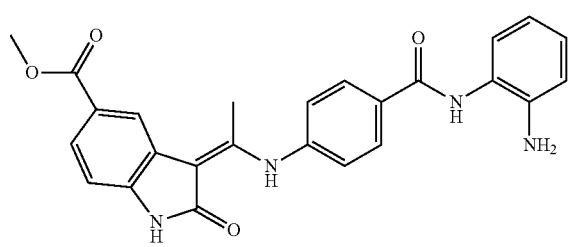

-continued

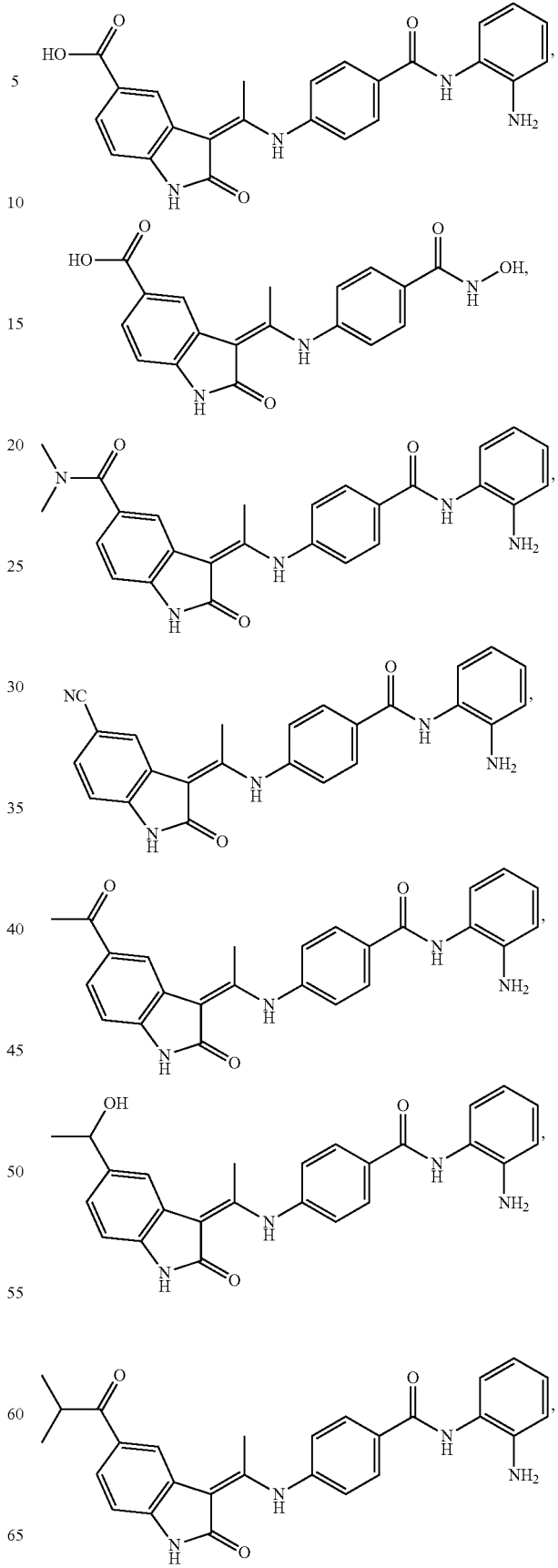

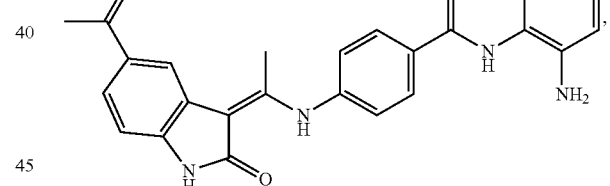

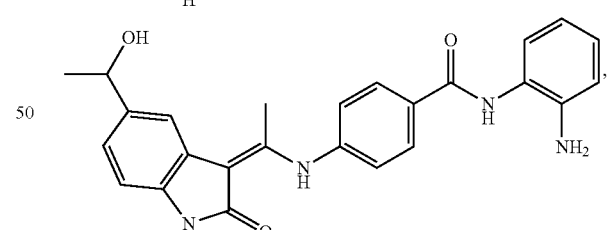

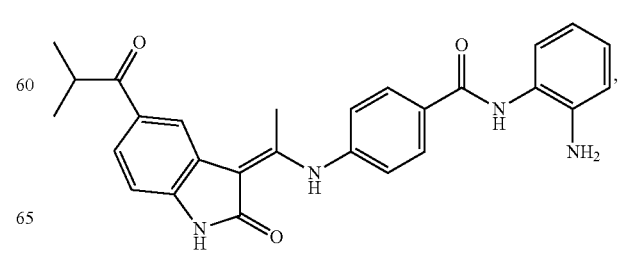

-continued

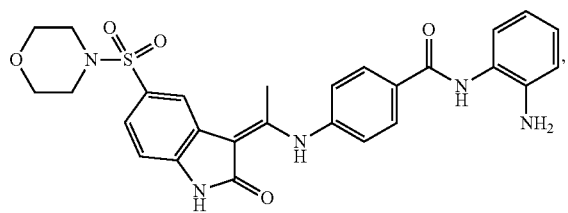
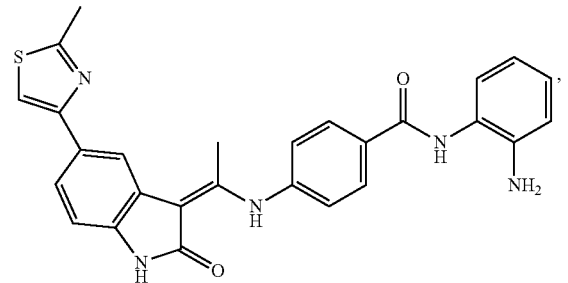
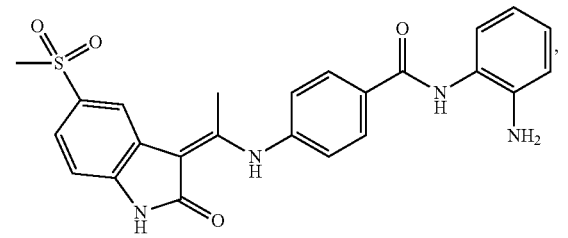
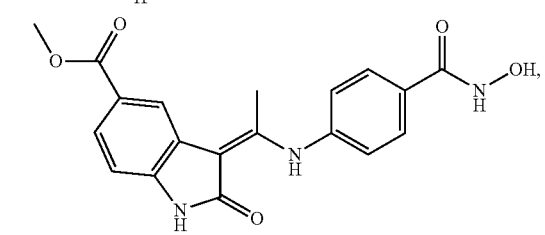
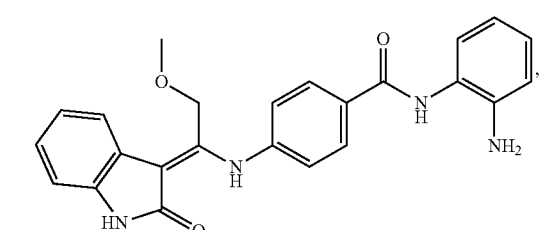
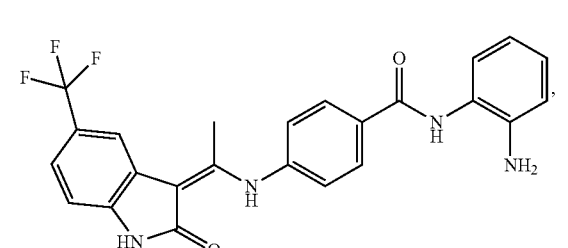
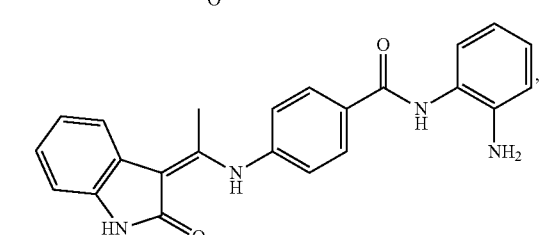

-continued

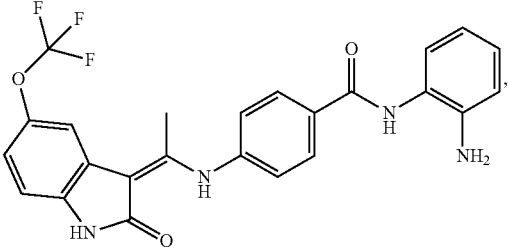
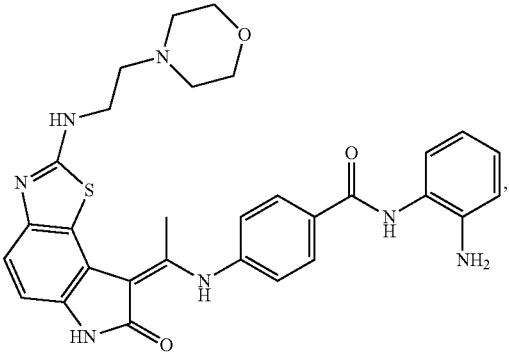
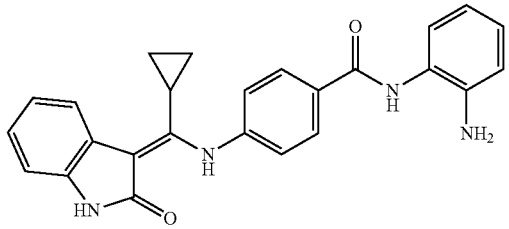

and pharmaceutically acceptable salts thereof.

Compound Preparation

A compound of the present invention such as those of Formulas (I), (I-a) and (I-b) can be prepared according to the schemes described below, but it shall be appreciated that modifications of the illustrated process or other process can also be used.

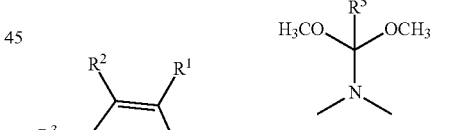
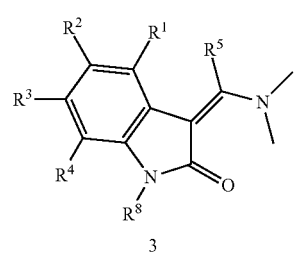

In a first synthetic step, oxindole compound 1 is condensed with diacetal compound 2 to yield exocyclic oxindole compound 3. Examples of diacetal compound 2 include dimethylformamide dimethyl acetal (DMFDMA, where $R^5$ is H) and N,N-dimethylacetamide dimethyl acetal, where $R^5$ is methyl.

Exocyclic intermediate compound 3 is reacted with aminoarylcarboxylate compound 4 to provide carboxylic acid compound 5, which is in turn converted to hydroxamate compound 6 or arylamide compound 8, where T is $NH_2$ or OH.

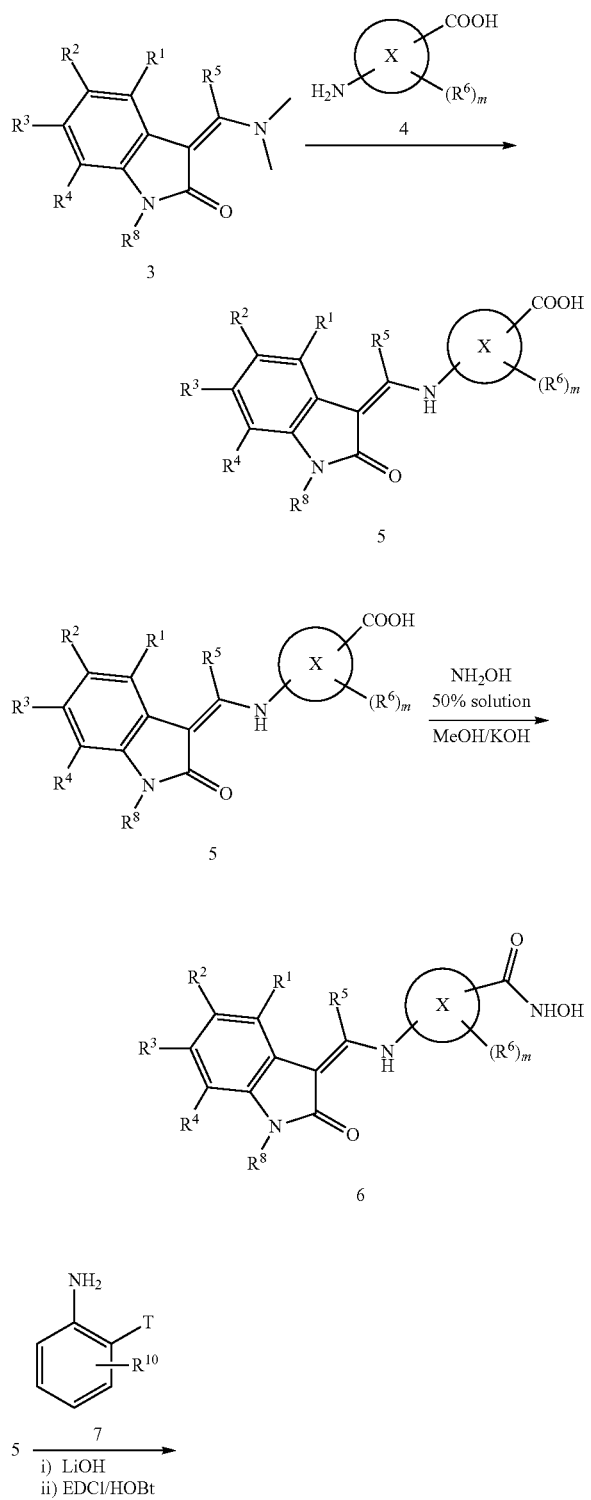

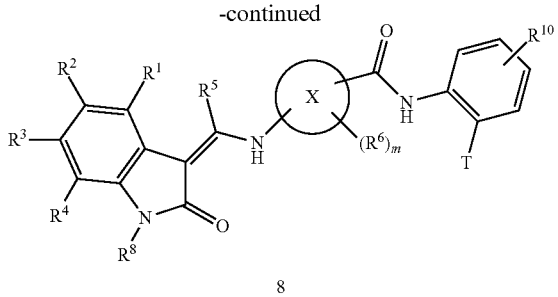

Starting materials and reagents can be readily synthesized or purchased from commercial sources. Reaction conditions for the transformations are well known. Non-limiting examples of synthetic conditions are given in the Examples.

In various embodiments, compounds described herein have HDAC and/or CDK inhibitory properties, as reflected in values of $IC_{50}$ in the range below 1 micromolar. In one embodiment, therefore, a compound of the invention is used in inhibiting HDAC and/or CDK enzymes such as, for example, mammalian HDAC and/or CDK. More specifically, a compound of the invention can be used to treat or ameliorate diseases mediated directly or indirectly by HDAC and/or CDK. Therefore, another aspect of the present invention is to provide a pharmaceutical composition comprising an effective amount of one or more compounds as described above.

In one embodiment of the invention, a pharmaceutical composition is provided comprising, in addition to one or more compounds described herein, at least one pharmaceutically-acceptable diluent, adjuvant, excipient, or carrier. The composition can take any suitable form for the desired route of administration. Where the composition is to be administered orally, any suitable orally deliverable dosage form can be used, including without limitation tablets, capsules (solid- or liquid-filled), powders, granules, syrups and other liquids, elixirs, inhalants, troches, lozenges, and solutions. Injectable compositions or intravenous infusions are also provided in the form of solutions, suspensions, and emulsions.

A pharmaceutical composition according to the present invention may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by HDAC and/or CDK. Examples of such active ingredients are, without limitation, agents to treat or inhibit cancer, Huntington's disease, cystic fibrosis, liver fibrosis, renal fibrosis, pulmonary fibrosis, skin fibrosis, Rheumatoid arthritis, diabetes, stroke, amyotrophic lateral sclerosis, cardiac hypertrophy, heart failure, or Alzheimer's disease.

In an embodiment, an additional therapeutic agent to be included is an anti-cancer agent. Examples of an anti-cancer agent include, but are not limited to, alkylating agents such as cyclophosphamide, dacarbazine, and cisplatin; antimetabolites such as methotrexate, mercaptopurine, thioguanine, fluorouracil, and cytarabine; plant alkaloids such as vinblastine, and paclitaxel; antitumor antibiotics such as doxorubicin, bleomycin, and mitomycin; hormones/antihormones such as prednisone, tamoxifen, and flutamide; other types of anticancer agents such as asparaginase, rituximab, trastuzumab, imatinib, retinoic acid and derivatives, colony-stimulating factors, amifostine, camptothecin, topotecan, thalidomide analogs such as lenalidomide, CDK inhibitor and other HDAC inhibitor such as histone deacetylase 1 inhibitors, histone deacetylase 2 inhibitors, histone deacetylase 3 inhibitors, histone deacetylase 4 inhibitors, histone deacetylase 5 inhibitors, histone deacetylase 6 inhibitors, histone deacetylase 7 inhibitors, histone deacetylase 8 inhibitors, histone deacetylase 9 inhibitors, histone deacetylase 10 inhibitors, and histone deacetylase 11 inhibitors. Yet another aspect of the present invention is to provide a method of inhibiting or treating diseases arising from abnormal cell proliferation and/or differentiation in animal, comprising administering to said animal a therapeutically effective amount of one or more compounds according to the present invention. In one embodiment, the method of inhibiting or treating disease comprises administering to an animal a composition comprising an effective amount of one or more compounds of the invention and a pharmaceutically-acceptable carrier. The composition to be administered may further contain a therapeutic agent such as anti-cancer agent.

A method of the present invention is particularly suitable for use with humans, but may be used with other animals, particularly mammals, such as, for example, non-human primates, companion animals, farm animals, laboratory animals, and wild and zoo animals.

A method of the present invention is particularly useful to treat diseases mediated directly or indirectly by HDAC and/or CDK since the compounds of the present invention have inhibitory activity against those molecules. In some embodiments, therefore, a method of the present invention is used in inhibiting or treating HDAC- and/or CDK-mediated diseases. Examples of such disease include, but are not limited to, cell proliferative diseases such as cancer, autosomal dominant disorders such as Huntington's disease, genetic related metabolic disorder such as cystic fibrosis, fibrosis such as liver fibrosis, renal fibrosis, pulmonary fibrosis and skin fibrosis, autoimmune diseases such as Rheumatoid arthritis, diabetes, acute and chronic neurological diseases such as stroke, amyotrophic lateral sclerosis, hypertrophy such as cardiac hypertrophy, heart failure including congestive heart failure, and Alzheimer's disease. In an embodiment, a method according to the present invention is applied to a patient with cancer, cystic fibrosis, or pulmonary fibrosis. In some embodiments, a method using a compound according to the present invention is used to treat or inhibit a cancer selected from bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer.

EXAMPLES

The following examples are merely illustrative, and do not limit this disclosure in any way.

Example 1

3-{1-[4-(2-Amino-phenylcarbamoyl)-phenylamino]-ethylidene}-2-oxo-2,3-dihydro-1H-indole-5-carboxylic acid methyl ester

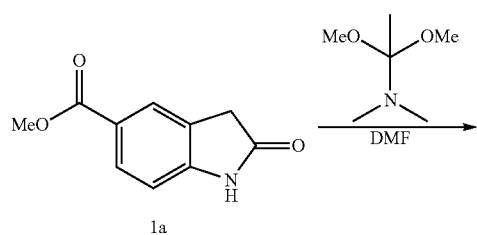

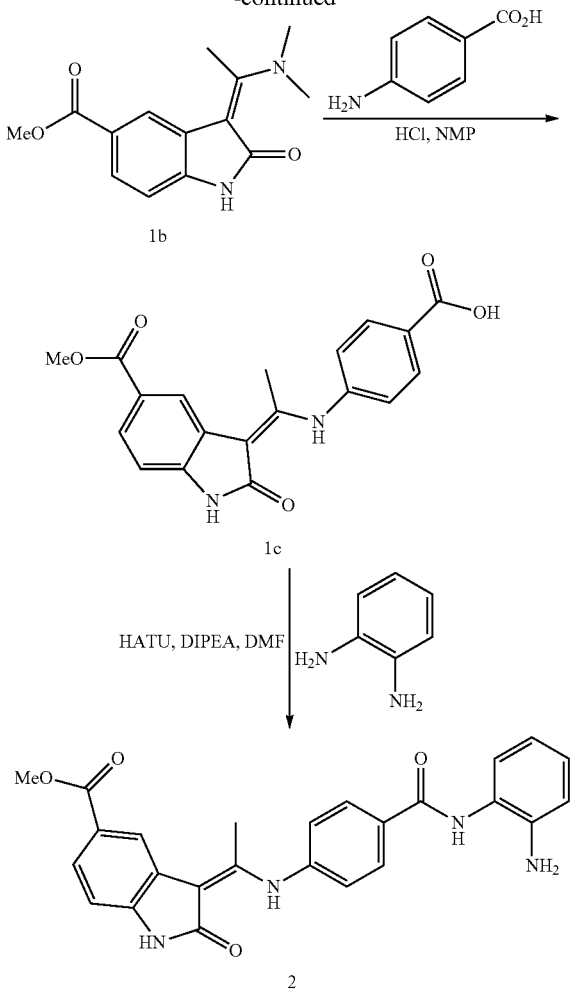

Preparation of Intermediate (Hereinafter "Int") 1b

To a suspension of Int-1a (1.05 g, 5.5 mmol) in dimethylformamide (DMF) (7.5 mL) was added N,N-dimethylacetamide-dimethyl acetal (1.2 mL, 7.14 mmol). The reaction mixture was stirred at room temperature for 1 hour and diluted with Et$_2$O (7.5 mL). The resulting solid was filtered, washed with ether, and dried to give Int-1b. MS found for C$_{14}$H$_{16}$N$_2$O$_3$ (m/z): 261.1 [M$^+$+1].

Preparation Int-1c

To a solution of Int-1b (350 mgs, 1.35 mmol) in N-methyl-2-pyrrolidone (NMP) (5 mL) were added 4-aminobenzoic acid (185 mgs, 1.35 mmol) and 4.0M HCl in dioxane (0.34 mL, 1.35 mmol). The reaction mixture was then heated in microwave (Emry's Optimizer) at 150° C. for 1 hour and diluted with water (20 mL). The resulting solid was filtered and washed with water and dried to give Int-1c. MS found for C$_{19}$H$_{16}$N$_2$O$_5$ (m/z): 353.0 [M$^+$+1].

Preparation of Compound 2

To Int-1c (243 mgs, 0.69 mmol) in DMF (7 mL) were added O-(7-azabenzotirazol-1-yl)-N,N,N',N'-tetramethyluronium hexafluorophosphate (HATU) (393 mgs, 1.04 mmol), 1,2-phenylenediamine (149 mgs, 1.38 mmol) and N,N-diisopropylethylamine (DIPEA) (0.5 mL, 2.76 mmol) and stirred at room temperature. After 16 hours, the reaction mixture was diluted with ethyl acetate and washed with 1N HCl. The organic layer was then concentrated in vacuo and diluted with water and acetonitrile and directly purified by preparative high performance liquid chromatography (HPLC), affording Compound 2, after lyophilization. MS found for $C_{25}H_{22}N_4O_4$ (m/z): 442.8 [M$^+$+1]. $^1$H NMR (400 MHz, dmso-d$_6$): δ 12.25 (s, 1H); 11.02 (s, 1H); 9.64 (s, 1H); 8.03 (d, J=8.4 Hz, 2H); 7.93 (s, 1H): 7.69 (m, 1H); 7.40 (d, J=8.4 Hz, 2H); 7.13 (d, J=7.6 Hz, 1H); 7.13 (d, J=7.6 Hz, 1H); 6.98 (m, 2H); 6.75 (m, 1H); 6.57 (t, J=7.6 Hz, 1H); 6.53 (brs, NH); 3.78 (s, 3H); 2.59 (s, 3H)

Example 2

3-{[4-(2-Amino-phenylcarbamoyl)-phenylamino]-methylene}-2-oxo-2,3-dihydro-1H-indole-5-carboxylic acid methyl ester

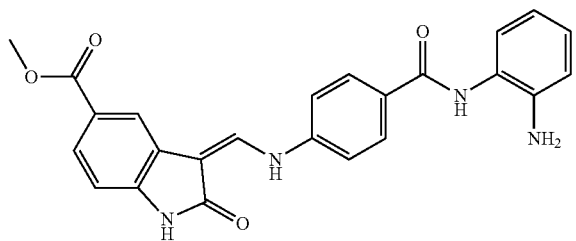 [SMILES: COC(=O)c1ccc2c(c1)/C(=C/Nc1ccc(C(=O)Nc3ccccc3N)cc1)C(=O)N2]

Preparation of Example 2

The title compound was prepared from N,N-dimethylformamide-di-tert-butyl acetal instead of N,N-dimethylacetamide-dimethyl acetal using a procedure similar to that of Example 1. MS found for $C_{24}H_{20}N_4O_4$ (m/z): 428.8 [M$^+$+1]. $^1$H NMR (400 MHz, dmso-d$_6$): δ 10.89 (s, 1H); 10.81 (s, 1H); 9.55 (s, 1H); 8.89 (d, J=12.4 Hz, 1H); 8.27 (s, 1H): 7.97 (d, J=8.4 Hz, 2H); 7.67 (m, 1H); 7.54 (d, J=8.4 Hz, 1H); 7.10 (d, J=8.0 Hz, 1H); 6.92-6.85 (m, 2H); 6.73 (d, J=7.6 Hz, 1H); 6.56 (t, J=7.6 Hz, 1H); 4.84 (brs, NH); 3.78 (s, 3H).

Example 3

N-(2-Amino-phenyl)-4-[1-(5-cyano-2-oxo-1,2-dihydro-indol-3-ylidene)-ethylamino]-benzamide

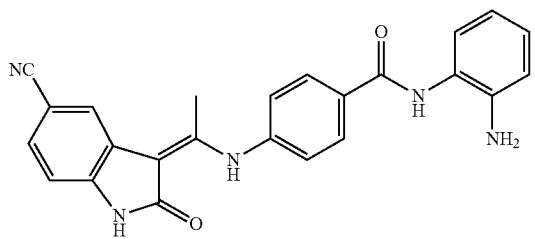 [SMILES: C/C(Nc1ccc(C(=O)Nc2ccccc2N)cc1)=C1/C(=O)Nc2ccc(C#N)cc21]

Preparation of Example 3

The title compound was prepared from 2-oxoindoline-5-carbonitrile instead of Int-1a of Example 1, using a procedure similar to that of Example 1. MS found for $C_{25}H_{22}N_4O_4$ (m/z): 409.9 [M$^+$+1]. $^1$H NMR (400 MHz, dmso-d$_6$): δ 12.28 (s, 1H); 11.09 (s, 1H); 9.63 (s, 1H); 8.02 (d, J=8.8 Hz, 2H); 7.78 (s, 1H): 7.48-7.44 (m, 5H); 7.30-7.25 (m, 3H); 7.05 (d, J=8.0 Hz, 1H); 2.62 (s, 3H).

Example 4

4-[1-(5-Acetyl-2-oxo-1,2-dihydro-indol-3-ylidene)-ethylamino]-N-(2-amino-phenyl)-benzamide

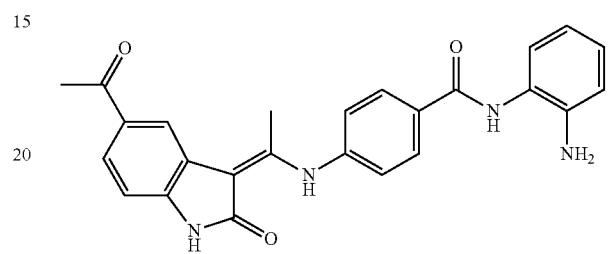

Preparation of Example 4

The title compound was prepared from 5-acetylindolin-2-one instead of Int-1a of Example 1, using a procedure similar to that of Example 1. MS found for $C_{25}H_{22}N_4O_3$ (m/z): 426.9 [M$^+$+1]. $^1$H NMR (400 MHz, dmso-d$_6$): δ 12.25 (s, 1H); 10.99 (s, 1H); 9.63 (s, 1H); 8.01 (d, J=8.4 Hz, 2H); 7.90 (s, 1H): 7.70 (d, J=8.0 Hz, 1H); 7.38 (d, J=8.4 Hz, 2H); 7.18 (d, J=7.6 Hz, 1H); 6.95 (m, 2H); 6.73 (d, J=8.0 Hz, 2H); 6.59 (t, J=7.6 Hz, 1H); 4.85 (brs, NH); 2.60 (s, 3H); 2.43 (s, 3H).

Example 5

N-(2-Amino-phenyl)-4-[1-(5-isobutyryl-2-oxo-1,2-dihydro-indol-3-ylidene)-ethylamino]-benzamide

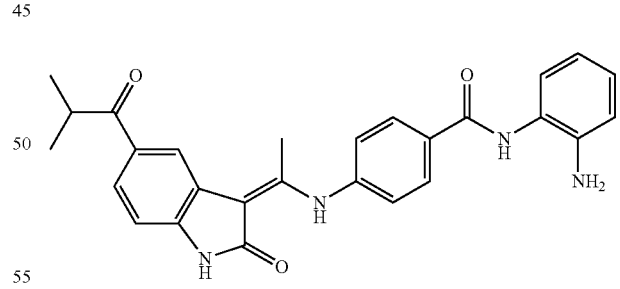

Preparation of Example 5

The title compound was prepared from 5-isobutyrylindolin-2-one instead of Int-1a of Example 1, using a procedure similar to that of Example 1. MS found for $C_{27}H_{26}N_4O_3$ (m/z): 454.9 [M$^+$+1]. $^1$H NMR (400 MHz, dmso-d$_6$): δ 12.28 (s, 1H); 11.04 (s, 1H); 9.69 (s, 1H); 8.07 (d, J=8.4 HZ, 2H); 7.97 (s, 1H); 7.78 (d, J=8.0 Hz, 1H); 7.44 (d, J=8.0 Hz, 2H): 7.17 (d, J=8.0 Hz, 1H); 7.02-6.95 (m, 2H); 6.79 (d, J=8.0 Hz, 1H); 6.61 (t, J=7.6 Hz, 1H); 4.91 (brs, NH); 3.71-3.64 (m, 1H); 2.66 (s, 3H); 1.12 (d, J=6.80 Hz, 6H).

Example 6

N-(2-Amino-phenyl)-4-{1-[5-(morpholine-4-sulfonyl)-2-oxo-1,2-dihydro-indol-3-ylidene]-ethylamino}-benzamide

Preparation of Example 6

The title compound was prepared from 5-(morpholinosulfonyl)indolin-2-one instead of Int-1a of Example 1, using a procedure similar to that of Example 1. MS found for $C_{27}H_{27}N_5O_5S$ (m/z): 534.4 [M$^+$1]. $^1$H NMR (400 MHz, dmso-d$_6$): δ 12.30 (s, 1H); 11.13 (s, 1H); 9.64 (s, 1H); 8.02 (d, J=8.4 Hz, 2H); 7.55 (s, 1H); 7.40-7.35 (m, 3H); 7.08 (d, J=8.4 Hz, 2H); 6.73 (d, J=8.0 Hz, 1H); 6.55 (t, J=7.6 Hz, 1H); 3.57-3.55 (m, 4H); 2.79-2.65 (m, 4H); 2.62 (s, 3H).

Example 7

N-(2-Amino-phenyl)-4-{1-[5-(2-methyl-thiazol-4-yl)-2-oxo-1,2-dihydro-indol-3-ylidene]-ethylamino}-benzamide

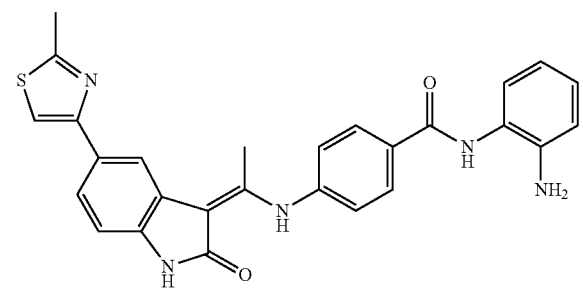

Preparation of Example 7

The title compound was prepared from 5-(2-methylthiazol-4-yl)indolin-2-one instead of Int-1a of Example 1, using a procedure similar to that of Example 1. MS found for $C_{27}H_{23}N_5O_2S$ (m/z): 482.3 [M$^+$+1]. $^1$H NMR (400 MHz, dmso-d$_6$): δ 8.07 (d, J=8.4 Hz, 2H); 7.96 (s, 1H); 7.76 (s, 1H); 7.65-7.62 (m, 1H); 7.43 (d, J=8.4 Hz, 2H); 7.17 (d, J=6.8 Hz, 1H); 6.98-6.93 (m, 2H); 6.79 (d, J=9.2 Hz, 1H); 6.58 (t, J=7.6 Hz, 1H); 4.91 (brs, NH); 2.70 (s, 3H); 2.67 (s, 3H).

Example 8

N-(2-Amino-phenyl)-4-[1-(5-methanesulfonyl-2-oxo-1,2-dihydro-indol-3-ylidene)-ethylamino]-benzamide

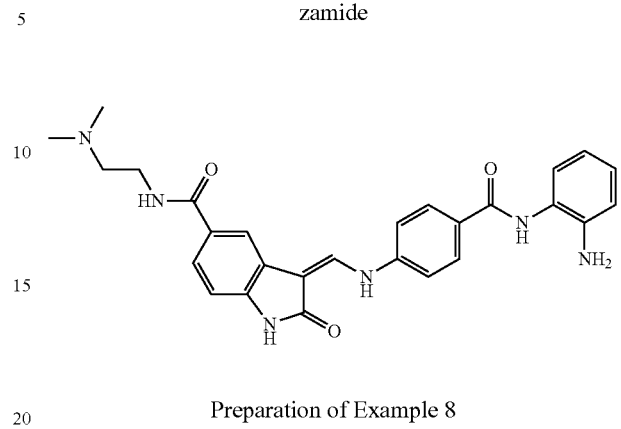

Preparation of Example 8

The title compound was prepared from 5-(methylsulfonyl)indolin-2-one instead of Int-1a of Example 1, using a procedure similar to that of Example 1. MS found for $C_{24}H_{22}N_4O_4S$ (m/z): 463.3 [M$^+$+1]. $^1$H NMR (400 MHz, dmso-d$_6$): δ 12.25 (s, 1H); 11.02 (s, 1H); 9.64 (s, 1H); 8.03 (d, J=8.8 Hz, 2H); 7.77 (s, 1H); 7.55 (d, J=8.4 Hz, 2H); 7.43 (d, J=8.4 Hz, 2H); 7.19-6.89 (m, 3H); 6.73 (d, J=8 Hz, 1H); 6.55 (t, J=7.6 Hz, 1H); 3.11 (s, 3H); 2.60 (s, 3H).

Using procedures similar to those described in Examples 1-8, the following compounds, Examples 9-13, were synthesized.

Example 9

3-{[4-(2-Amino-phenylcarbamoyl)-phenylamino]-methylene}-2-oxo-2,3-dihydro-1H-indole-5-carboxylic acid (2-dimethylamino-ethyl)-amide

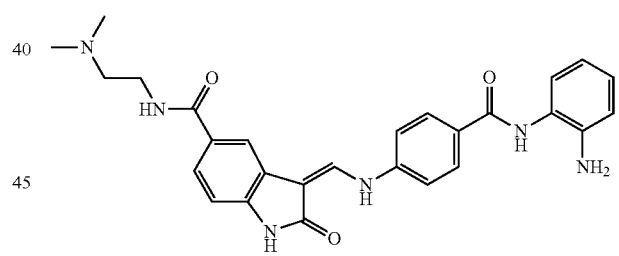

Example 10

3-{1-[4-(2-Amino-phenylcarbamoyl)-phenylamino]-ethylidene}-2-oxo-2,3-dihydro-1H-indole-5-carboxylic acid

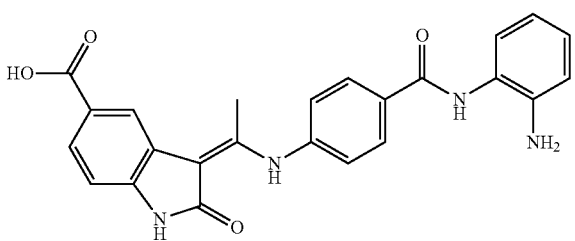

Example 11

3-[1-(4-Hydroxycarbamoyl-phenylamino)-ethylidene]-2-oxo-2,3-dihydro-1H-indole-5-carboxylic acid methyl ester

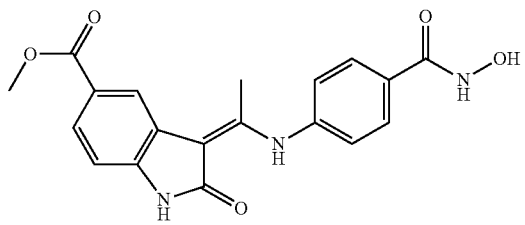

Example 12

3-{1-[4-(2-Amino-phenylcarbamoyl)-phenylamino]-ethylidene}-2-oxo-2,3-dihydro-1H-indole-5-carboxylic acid dimethylamide

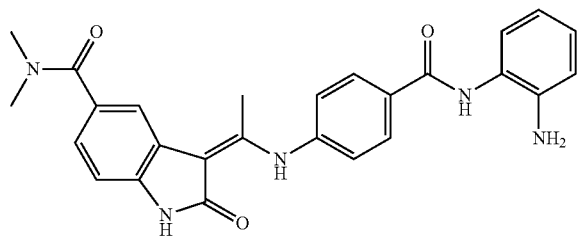

Example 13

N-(2-Amino-phenyl)-4-{1-[5-(1-hydroxy-ethyl)-2-oxo-1,2-dihydro-indol-3-ylidene]-ethylamino}-benzamide

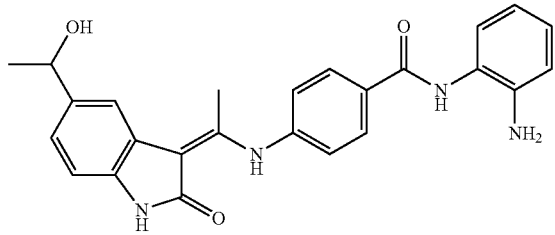

Example 14

Biological Assays

HDAC inhibitory activity of the compound of Example 1 was measured by two types of assays in which HDAC 1 was used as a target molecule. The first assay was carried out without preincubation after addition of the enzyme. The test compound was suspended in and titrated in dimethyl sulfoxide (DMSO). It was then spotted into a 384-well test plate. The enzyme, HDAC 1, was diluted in assay buffer containing 25 mM Tris-HCl (pH 8.0), 137 mM NaCl, 2.7 mM KCl, and 0.01% Tween-20 and added to the pre-spotted compound. The peptide substrate containing a fluorophore/quencher pair was diluted in the same assay buffer and added to the compound/enzyme mix initiating the reaction. The reaction incubated at room temperature for about 45 minutes. A concentrated developer solution was diluted in the assay buffer, and added to the reaction. The reaction was incubated at room temperature for about 15 minutes and relative fluorescence was read on an instrument reader.

The second assay is similar to the first assay described above, except that preincubation is carried out for about 3 hours after the enzyme is introduced. The test compound was suspended in, and titrated in DMSO. It was then spotted into a 384-well test plate. The enzyme, HDAC 1, was diluted in the same assay buffer as used in the previous assay and added to the pre-spotted compound. The enzyme/compound mix was incubated at room temperature for about 3 hours. The peptide substrate containing a fluorophore/quencher pair was diluted in the assay buffer and added to the compound/enzyme mix initiating the reaction. The reaction incubated at room temperature for 45 minutes. A concentrated developer solution was diluted in the assay buffer, and added to the reaction. The reaction was incubated at room temperature for about 15 minutes and relative fluorescence was read on an instrument reader.

The following table shows $IC_{50}$ data for the compound tested with the protocols described above. Where two numbers are given, the values are reported for measurements on two different lots of the compound.

TABLE 1

| | $IC_{50}$ of HDAC inhibitor compound | |
|---|---|---|
| Compound | HDAC 1 inhibitory activity ($IC_{50}$ [µM]) (3-hour preincubation) | CDK2 ($IC_{50}$ [µM]) |
| Example 1 | 0.033 | 0.043 |
| Example 2 | 0.170 | 0.07 |
| Example 3 | 0.029, 0.021 | 0.01, 0.02 |
| Example 4 | 0.064, 0.030 | 0.01, 0.01 |
| Example 5 | 0.335 | 0.02 |
| Example 6 | 0.186 | 0.52 |
| Example 7 | 0.232 | >40 |
| Example 8 | 0.100 | 0.13 |
| Example 9 | 0.063 | 0.25 |
| Example 10 | 0.181 | 0.44 |
| Example 11 | 0.635 | >40 |
| Example 12 | 0.071 | 0.34 |
| Example 13 | 0.036 | 1.01 |

The results indicate that the compounds have inhibitory activity against HDAC and/or CDK and thus can be useful to treat or inhibit diseases caused by abnormal activities of HDAC and/or CDK.

All patents and publications cited herein are incorporated by reference into this application in their entirety.

What is claimed is:

1. A compound selected from those of Formula (I) and pharmaceutically acceptable salts thereof:

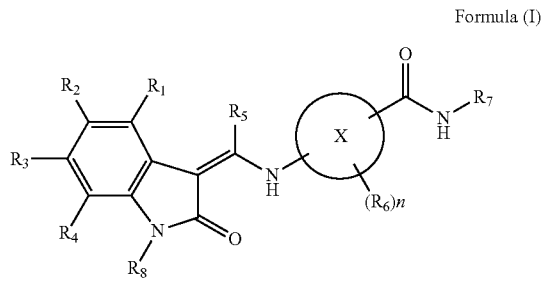

Formula (I)

wherein $R^1$, $R^2$, $R^3$ and $R^4$ are independently selected from the group consisting of H, halo, nitro, cyano, hydroxy, hydroxyalkyl, haloalkyl, haloalkoxy, amino, aminoalkyl, azido, carboxyl, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{1-10}$ alkanoyloxy, N-($C_{1-10}$ alkyl)amino, N-(heterocyclyl $C_{1-10}$ alkyl)amino, N,N-($C_{1-10}$ alkyl)$_2$-amino, $C_{1-10}$ alkanoylamino, N-($C_{1-10}$ alkyl)carbamoyl, N,N-($C_{1-10}$ alkyl)$_2$-carbamoyl, $C_{1-10}$ alkyl-S(O), wherein a is 0, 1 or 2, $C_{1-10}$ alkoxycarbonyl, $NH_2$—S(O)$_2$NH—, N-($C_{1-10}$ alkyl)sulphamoyl, N,N-($C_{1-10}$ alkyl)$_2$sulphamoyl, aryl, aryloxy, arylthio, heteroaryl, heteroaryloxy, cycloalkyl, cycloalkyloxy, heterocyclyl, heterocyclyl(C=O)—, heterocyclyloxy and heterocyclylthio; wherein each of $R^1$, $R^2$, $R^3$ and $R^4$ is optionally substituted by one or more A, or $R^3$ and $R^4$ are as defined above, and $R^1$ and $R^2$ together form a cyclic moiety to make a fused ring together with the oxindole ring drawn in Formula (I), wherein the cyclic moiety optionally contains one or more heteroatom selected from N, O and S and the cyclic moiety itself is optionally substituted by one or more substituents selected from $R^1$, $R^2$, $R^3$ and $R^4$ groups, each of which is optionally substituted by one or more A; or $R^1$ and $R^4$ are as defined above, and $R^2$ and $R^3$ together form a cyclic moiety to make a fused ring together with the oxindole ring drawn in Formula (I), wherein the cyclic moiety optionally contains one or more heteroatom selected from N, O and S and the cyclic moiety itself is optionally substituted by one or more substituents selected from $R^1$, $R^2$, $R^3$ and $R^4$ groups, each of which is optionally substituted by one or more A;

$R^5$ is selected from the group consisting of H, halo, haloalkyl, amino, $C_{1-10}$ alkyl, N—($C_{1-10}$ alkyl)amino and N,N-($C_{1-10}$ alkyl)$_2$ amino, alkoxyalkyl, alkylaminoalkyl, and cycloalkyl, wherein $R^5$ is optionally substituted by one or more B;

X is phenyl, 5-membered heteroaryl, or 6-membered heteroaryl, wherein the heteroaryl contains one or more heteroatoms selected from N, S and O;

$R^6$ represents one or more non-hydrogen substituents selected from halo and methyl;

n is 0, 1, 2, 3, or 4;

$R^7$ is hydroxy, aryl or heteroaryl, wherein aryl or heteroaryl are substituted with —$NH_2$ or —OH and aryl or heteroaryl is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl;

$R^8$ is H, alkyl, alkanoyl, or cycloalkyl; and

A and B are independently selected from halo, nitro, cyano, hydroxy, hydroxyalkyl, haloalkyl, haloalkoxy, amino, azido, carboxyl, carbamoyl, mercapto, oxo, sulphamoyl, $C_{1-10}$ alkyl, $C_{2-10}$ alkenyl, $C_{2-10}$ alkynyl, $C_{1-10}$ alkoxy, $C_{1-10}$ alkoxyalkyl, $C_{1-10}$ alkanoyl, $C_{1-10}$ alkanoyloxy, N-(heterocyclyl $C_{1-10}$ alkyl)amino, N-($C_{1-10}$ alkyl) amino, N,N-($C_{1-10}$ alkyl)$_2$amino, $C_{1-10}$ alkanoylamino, N-($C_{1-10}$ alkyl)carbamoyl, N,N-($C_{1-10}$ alkyl)$_2$carbamoyl, $C_{1-10}$ alkyl-S(O)$_a$ wherein a is 0, 1 or 2, $C_{1-10}$ alkoxycarbonyl, N-($C_{1-10}$ alkyl)sulphamoyl, N,N-($C_{1-10}$ alkyl)$_2$sulphamoyl, $H_2NS(O)_2NH$—, N-($C_{1-10}$ alkyl)NHS(O)$_2$NH—, N,N-($C_{1-10}$ alkyl)$_2$NS(O)$_2$NH—, aryl, aryloxy, arylthio, heteroaryl, heteroaryloxy, cycloalkyl, cycloalkyloxy, heterocyclyl, heterocyclyl (C=O)—, heterocyclyloxy and heterocyclylthio.

2. The compound of claim 1, wherein at least two of $R^1$, $R^2$, $R^3$ and $R^4$ are hydrogen and each non-hydrogen $R^1$, $R^2$, $R^3$ and $R^4$ is selected from chloro, fluoro, bromo, methyl, ethyl, propyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethylaminomethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;

$R^5$ is H, methyl, ethyl or trifluoromethyl; and

X is phenyl or 5-membered heteroaryl.

3. The compound of claim 1 selected from those of Formula (I-a) and pharmaceutically acceptable salts thereof:

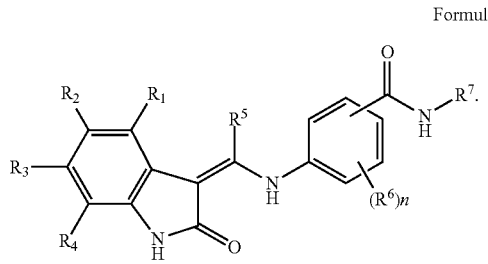

Formula (I-a)

4. The compound of claim 3, wherein at least two of $R^1$, $R^2$, $R^3$ and $R^4$ are H, and each non-hydrogen $R^1$, $R^2$, $R^3$ and $R^4$ is independently selected from chloro, fluoro, bromo, methyl, ethyl, propyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminomethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy; $R^5$ is H, alkyl or haloalkyl; $R^6$ is fluoro, chloro, bromo, or methyl and n is 0 or 1; and $R^7$ is hydroxyl, aryl or heteroaryl, wherein aryl or heteroaryl are substituted with —$NH_2$ or —OH at a ring position adjacent to attachment of the —CONH-moiety, and $R^7$ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

5. The compound of claim 3 which is selected from the group consisting of:

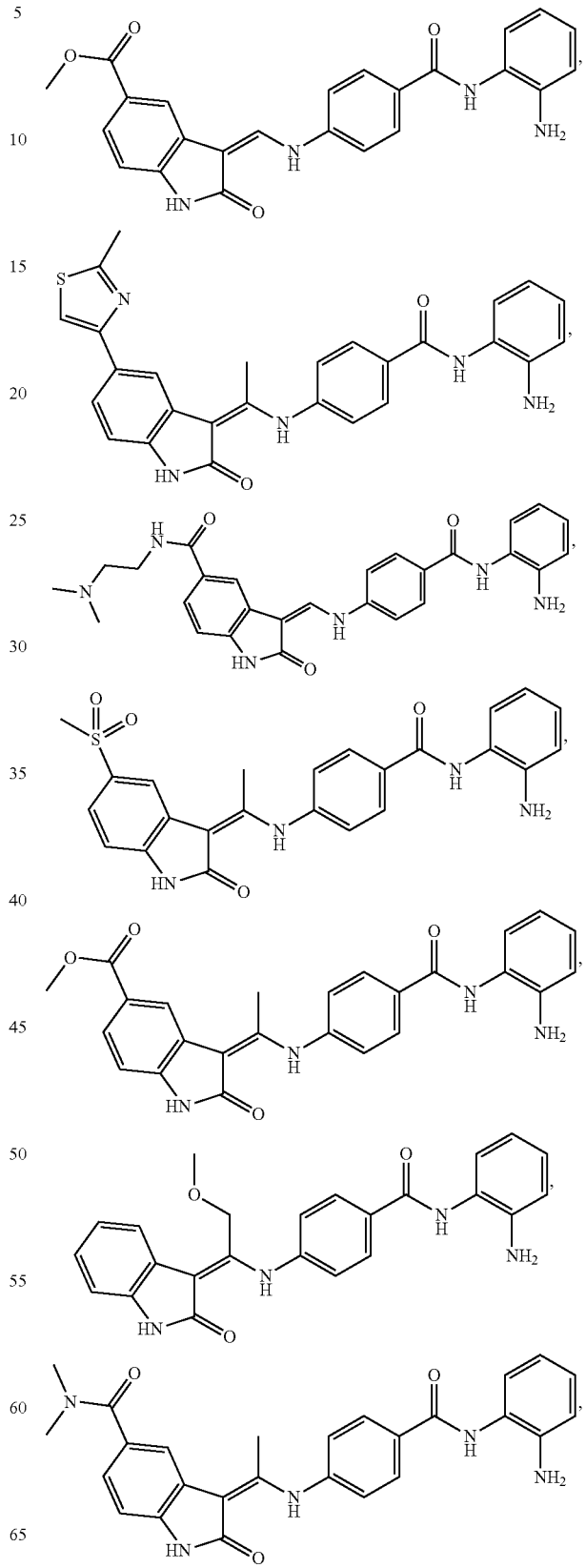

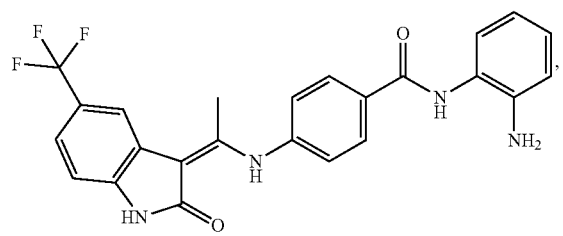
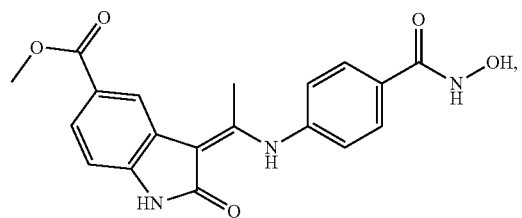
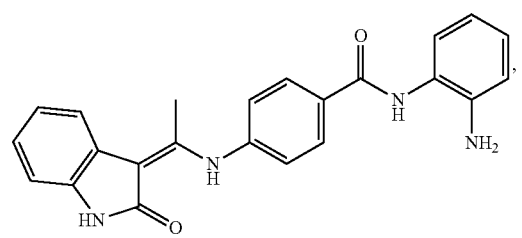
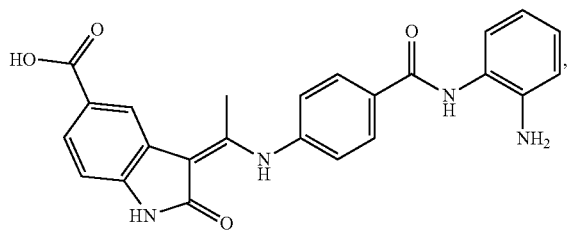
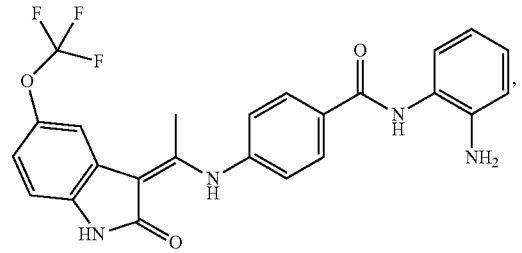
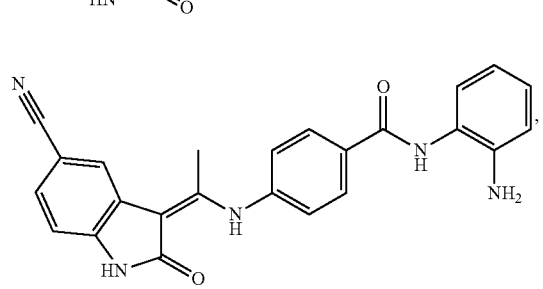
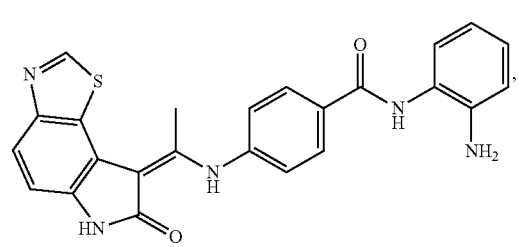
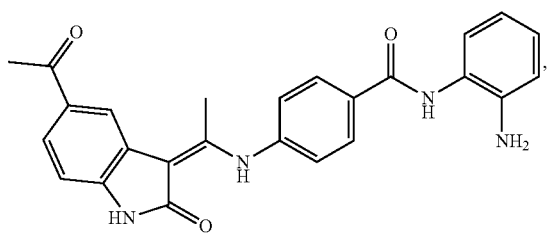
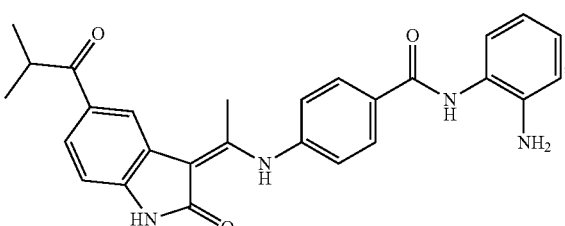
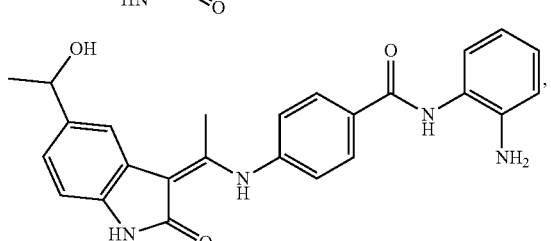
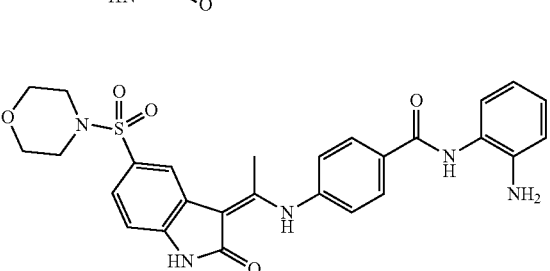
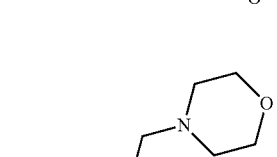
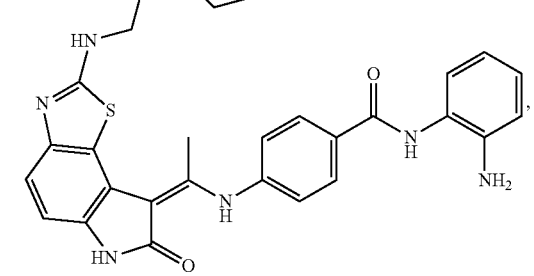
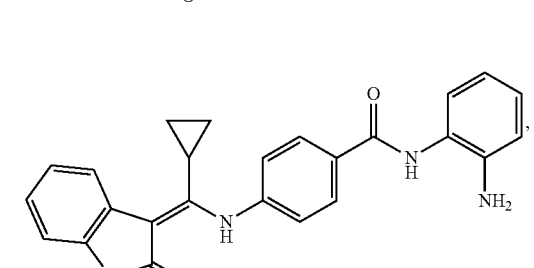
and pharmaceutically acceptable salts thereof.

6. The compound of claim 3 which is selected from the group consisting of:
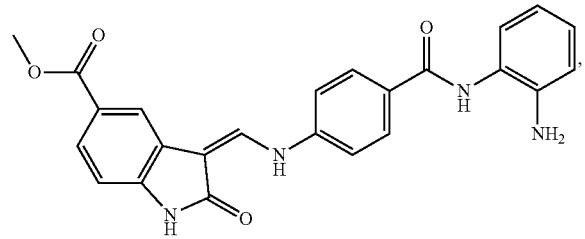
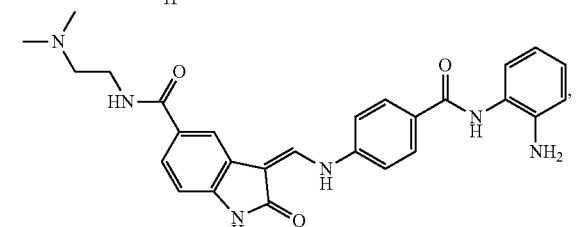
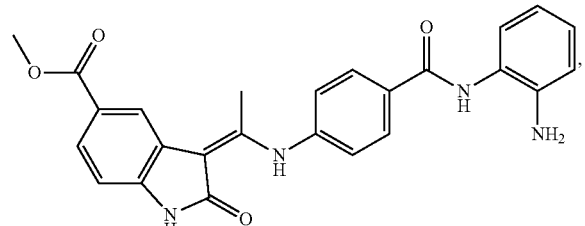
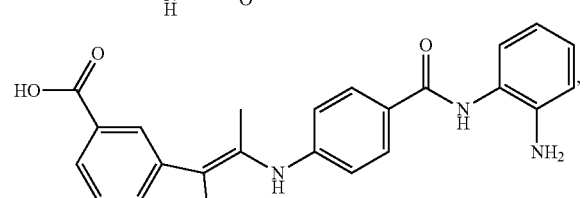
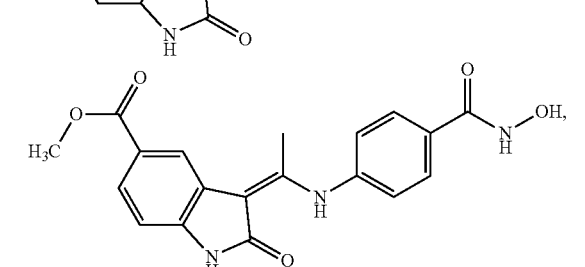
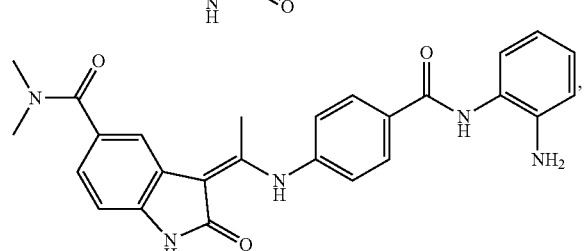
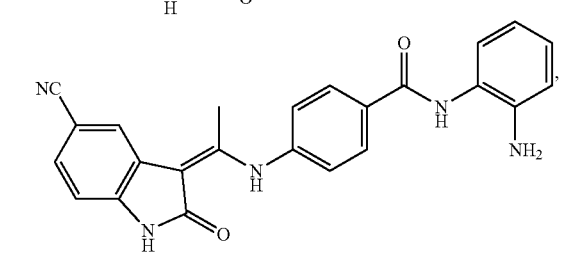
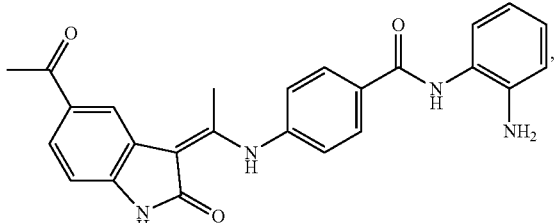
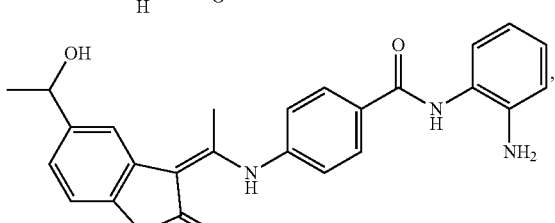
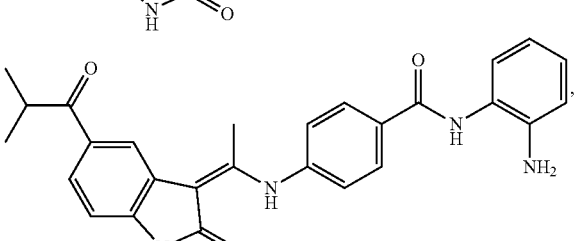
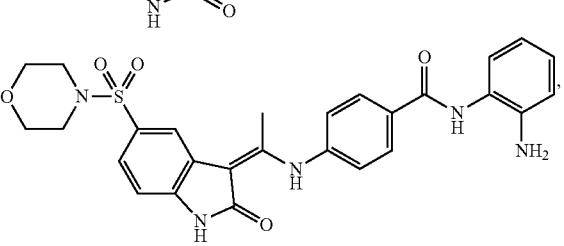
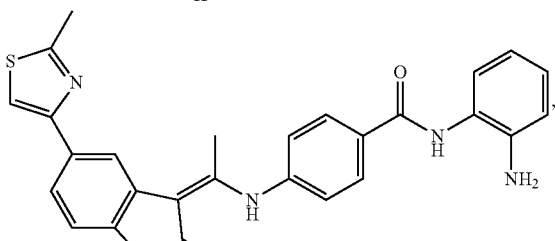
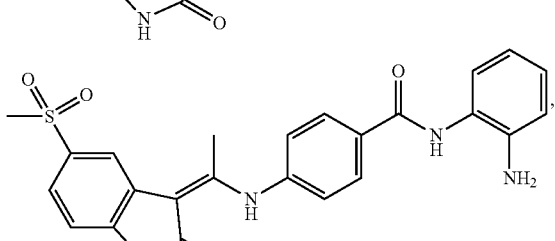
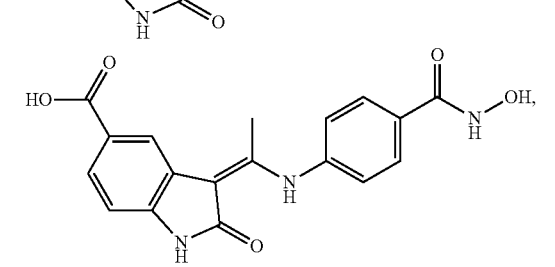
and pharmaceutically acceptable salts thereof.

7. The compound of claim 1 selected from those of Formula (I-b) and pharmaceutically acceptable salts thereof:

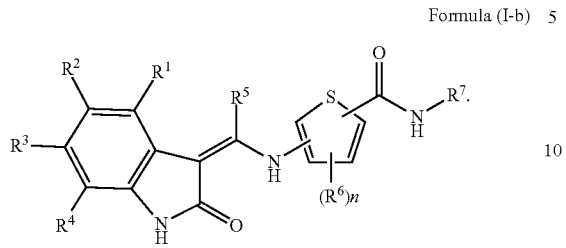

Formula (I-b)

8. The compound of claim 7, wherein at least two of $R^1$, $R^2$, $R^3$ and $R^4$ are H, and each non-hydrogen $R^1$, $R^2$, $R^3$ and $R^4$ is independently selected from chloro, fluoro, bromo, methyl, ethyl, propyl, methoxy, ethoxy, acetyl, carboxyl, methylcarboxyl, cyano, methoxymethyl, ethoxyethyl, propoxyethyl, methoxyethoxy, trifluoromethyl, hydroxyethoxy, dimethylamino, diethylamino, dimethylaminomethyl, dimethylaminoethyl, diethylaminomethyl, dimethylaminoethoxy, dimethylaminocarbonyl, dimethylaminoethylamide, trifluoromethoxymethyl, trifluoroethoxymethyl, isopropylcarbonyl, 1-hydroxyethyl, 3-oxetanoxy, trifluoroethylaminomethyl, N-methyl-N-methoxyethyl-aminomethyl, cyclopropanylmethyl, cyclopropyl, cyclobutoxy, 1-cyclopropanylethoxy, cyclopropanylmethylaminomethyl, 4-methylpiperazin-1-carbonyl, isoindolin-2-yl, N-methoxyethylcarbamoyl, N-(morpholin-4-yl)-ethylcarbamoyl, dimethylaminoethylamino, N,N-dimethylaminoethylcarbamoyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, methanesulfonyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, thiazol-4-yl, 2-methyl-thiazol-4-yl, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-4-ylsulfonyl, morpholin-2-ylethoxy, morpholin-3-ylethoxy and morpholin-4-ylethoxy;
$R^5$ is H, alkyl or haloalkyl;

$R^6$ is fluoro, chloro, bromo, or methyl and n is 0 or 1; and
$R^7$ is hydroxyl, aryl or heteroaryl, wherein aryl or heteroaryl are substituted with —$NH_2$ or —OH at a ring position adjacent to attachment of the —CONH-moiety, and $R^7$ is optionally further substituted with one or more groups selected from amino, halo, alkyl, alkenyl, alkynyl, haloalkyl, cycloalkyl, heterocyclyl, aryl, haloaryl, haloheterocyclyl, wherein alkyl, alkenyl, or alkynyl is optionally further substituted with one or more groups selected from halo, hydroxy, alkyl, haloalkyl and cycloalkyl.

9. A compound selected from those of Formula (II) and pharmaceutically acceptable salts thereof:

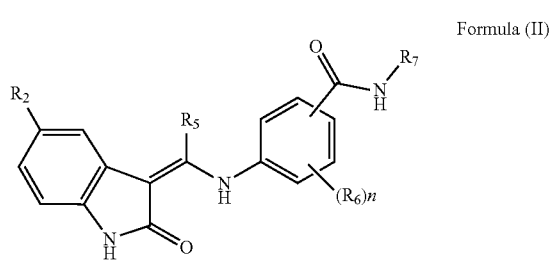

Formula (II)

wherein
$R^2$ is selected from the group consisting of H, hydroxy, $C_{1-10}$ alkyl, $C_{1-10}$ alkanoyl, $C_{1-10}$ methoxy, hydroxyalkyl, halo, haloalkyl, haloalkoxy, N,N-($C_{1-10}$ alkyl)$_2$aminoalkyl, cyano, carboxyl, methylcarboxyl, N,N-($C_{1-10}$ alkyl)$_2$amide, N,N-($C_{1-10}$ alkyl)$_2$-aminoethylaminocarbonyl, morpholinylsulfonyl, alkylthiazolyl, $C_{1-10}$ alkyl-S(O)a wherein a is 0, 1 or 2, morpholinylmethyl and pyrrolidinylmethyl;
$R^5$ is H or alkyl;
$R^6$ is halo and n is 0 or 1; and
$R^7$ is hydroxy, aryl or heteroaryl, wherein aryl or heteroaryl are substituted with —$NH_2$ at a ring position adjacent to attachment of the —CONH-moiety.

10. A pharmaceutical composition comprising an of one or more compounds of claim 1 and a pharmaceutically-acceptable carrier.

11. The pharmaceutical composition according to claim 10, further comprising one or more anti-cancer agents.

12. The pharmaceutical composition according to claim 11, wherein the one or more anti-cancer agents is selected from the group consisting of cyclophosphamide, dacarbazine, cisplatin, methotrexate, mercaptopurine, thioguanine, fluorouracil, cytarabine, vinblastine, paclitaxel, doxorubicin, bleomycin, mitomycin, prednisone, tamoxifen, flutamide, asparaginase, rituximab, trastuzumab, imatinib, retinoic acid, colony-stimulating factor, amifostine, lenalidomide, HDAC inhibitor, CDK inhibitor, camptothecin and topotecan.

* * * * *